(12) United States Patent
Kashyap et al.

(10) Patent No.: US 7,884,933 B1
(45) Date of Patent: Feb. 8, 2011

(54) APPARATUS AND METHOD FOR DETERMINING ANALYTE CONCENTRATIONS

(75) Inventors: Dheerendra Kashyap, Overland Park, KS (US); Craig Seyl, Olathe, KS (US); Carl Mayer, Overland Park, KS (US); John Ellenz, Olathe, KS (US)

(73) Assignee: Revolutionary Business Concepts, Inc., Lenexa, KS (US)

( * ) Notice: Subject to any disclaimer, the term of this patent is extended or adjusted under 35 U.S.C. 154(b) by 0 days.

(21) Appl. No.: 12/860,569

(22) Filed: Aug. 20, 2010

Related U.S. Application Data

(60) Provisional application No. 61/331,645, filed on May 5, 2010.

(51) Int. Cl.
*G01N 21/00* (2006.01)

(52) U.S. Cl. .......................... 356/338; 356/342

(58) Field of Classification Search ... 356/237.1–241.6, 356/242.1–243.8, 426–431, 600–640
See application file for complete search history.

(56) References Cited

U.S. PATENT DOCUMENTS

| | | |
|---|---|---|
| 4,223,680 A | 9/1980 | Jobsis |
| 4,570,638 A | 2/1986 | Stoddart et al. |
| 4,655,225 A | 4/1987 | Dahne et al. |
| 4,671,273 A | 6/1987 | Lindsey |
| 4,768,516 A | 9/1988 | Stoddart et al. |
| 4,817,623 A | 4/1989 | Stoddart et al. |
| 4,884,891 A | 12/1989 | Borsboom |
| 4,895,145 A | 1/1990 | Joffe et al. |
| 4,911,167 A | 3/1990 | Corenman et al. |
| 4,934,372 A | 6/1990 | Corenman et al. |
| 4,972,331 A | 11/1990 | Chance |
| 5,028,787 A | 7/1991 | Rosenthal et al. |
| 5,099,842 A | 3/1992 | Mannheimer et al. |
| 5,139,025 A | 8/1992 | Lewis et al. |
| 5,213,105 A | 5/1993 | Gratton et al. |
| 5,216,598 A | 6/1993 | Branstetter et al. |
| 5,217,013 A | 6/1993 | Lewis et al. |

(Continued)

OTHER PUBLICATIONS

Al-Rawl et al. "Evaluation of a Near-Infrared Spectrometer (NIRO 300) for the Detection of Intracranial Oxygenation Changes in the Adult Head." Stroke: Journal of the American Heart Association, vol. 32; pp. 2492-2500; Nov. 2001.

(Continued)

*Primary Examiner*—Gregory J Toatley
*Assistant Examiner*—Jarreas C Underwood
(74) *Attorney, Agent, or Firm*—Hovey Williams LLP

(57) ABSTRACT

An apparatus and method for determining an analyte concentration of a sample, such as a tissue sample. The apparatus may comprise an emitter, close proximity detectors laterally located less than about 2 mm away from the emitter, and far away detectors laterally located greater than about 0.5 cm away from the emitter. A plurality of wavelengths may be sent from the emitter to the sample, reflected off of the sample, and received by the detectors. The reflectance value measured by the close proximity detectors may be used to calculate one or more scattering coefficients. The reflectance value measured by the far away detectors may be compared with a reflectance value calculated using the scattering coefficients in a numerical inversion of a diffusion model to determine the analyte concentration of the sample.

20 Claims, 13 Drawing Sheets

U.S. PATENT DOCUMENTS

| | | | |
|---|---|---|---|
| 5,222,496 A | 6/1993 | Clarke et al. | |
| 5,226,417 A | 7/1993 | Swedlow et al. | |
| 5,251,632 A | 10/1993 | Delpy | |
| 5,253,646 A | 10/1993 | Delpy et al. | |
| 5,284,139 A | 2/1994 | Khalil et al. | |
| 5,284,149 A | 2/1994 | Dhadwal et al. | |
| 5,297,548 A | 3/1994 | Pologe | |
| 5,323,010 A | 6/1994 | Gratton et al. | |
| 5,337,745 A | 8/1994 | Benaron | |
| 5,349,961 A | 9/1994 | Stoddart et al. | |
| 5,351,685 A | 10/1994 | Potratz | |
| 5,353,790 A | 10/1994 | Jacques et al. | |
| 5,353,799 A | 10/1994 | Chance | |
| 5,379,764 A | 1/1995 | Barnes et al. | |
| 5,402,777 A | 4/1995 | Warring et al. | |
| 5,402,778 A | 4/1995 | Chance | |
| 5,419,321 A * | 5/1995 | Evans | 600/407 |
| 5,441,054 A | 8/1995 | Tsuchiya | |
| 5,465,714 A | 11/1995 | Scheuing | |
| 5,477,853 A | 12/1995 | Farkas et al. | |
| 5,482,034 A | 1/1996 | Lewis et al. | |
| 5,492,118 A * | 2/1996 | Gratton et al. | 600/316 |
| 5,494,032 A | 2/1996 | Robinson et al. | |
| 5,497,769 A | 3/1996 | Gratton et al. | |
| 5,513,642 A | 5/1996 | Ostrander | |
| 5,517,987 A | 5/1996 | Tsuchiya | |
| 5,548,604 A | 8/1996 | Toepel | |
| 5,551,472 A | 9/1996 | McBrayer, Jr. et al. | |
| 5,553,615 A | 9/1996 | Carim et al. | |
| 5,553,616 A | 9/1996 | Ham et al. | |
| 5,582,169 A | 12/1996 | Oda et al. | |
| 5,584,296 A | 12/1996 | Cui et al. | |
| 5,630,423 A | 5/1997 | Wang et al. | |
| 5,632,273 A * | 5/1997 | Suzuki | 600/310 |
| 5,657,754 A | 8/1997 | Rosencwaig | |
| 5,687,730 A | 11/1997 | Doiron et al. | |
| 5,697,367 A | 12/1997 | Lewis et al. | |
| 5,746,206 A | 5/1998 | Mannheimer | |
| 5,746,210 A | 5/1998 | Benaron et al. | |
| 5,769,785 A | 6/1998 | Diab et al. | |
| 5,770,454 A | 6/1998 | Essenpreis et al. | |
| 5,772,587 A | 6/1998 | Gratton et al. | |
| 5,787,572 A | 8/1998 | Toms et al. | |
| 5,792,051 A | 8/1998 | Chance | |
| 5,800,350 A | 9/1998 | Coppleson et al. | |
| 5,818,048 A | 10/1998 | Sodickson et al. | |
| 5,820,558 A | 10/1998 | Chance | |
| 5,825,488 A | 10/1998 | Kohl et al. | |
| 5,853,364 A | 12/1998 | Baker, Jr. et al. | |
| 5,853,370 A | 12/1998 | Chance et al. | |
| 5,860,919 A | 1/1999 | Kiani-Azarbayjany et al. | |
| 5,879,294 A | 3/1999 | Anderson et al. | |
| 5,885,213 A | 3/1999 | Richardson et al. | |
| 5,902,235 A * | 5/1999 | Lewis et al. | 600/323 |
| 5,931,779 A | 8/1999 | Arakaki et al. | |
| 5,995,856 A | 11/1999 | Mannheimer et al. | |
| 6,006,119 A | 12/1999 | Soller et al. | |
| 6,026,314 A | 2/2000 | Amerov et al. | |
| 6,058,324 A | 5/2000 | Chance | |
| 6,061,582 A | 5/2000 | Small et al. | |
| 6,067,462 A | 5/2000 | Diab et al. | |
| 6,078,833 A | 6/2000 | Hueber | |
| 6,094,592 A | 7/2000 | Yorkey et al. | |
| 6,095,974 A | 8/2000 | Shemwell et al. | |
| 6,104,938 A | 8/2000 | Huiku et al. | |
| 6,115,621 A | 9/2000 | Chin | |
| 6,138,046 A | 10/2000 | Dalton | |
| 6,146,375 A | 11/2000 | Juhasz et al. | |
| 6,151,516 A | 11/2000 | Kiani-Azarbayjany et al. | |
| 6,157,850 A | 12/2000 | Diab et al. | |
| 6,163,715 A | 12/2000 | Larsen et al. | |
| 6,192,260 B1 | 2/2001 | Chance | |
| 6,192,261 B1 | 2/2001 | Gratton et al. | |
| 6,195,574 B1 | 2/2001 | Kumar et al. | |
| 6,216,021 B1 | 4/2001 | Franceschini et al. | |
| 6,263,222 B1 | 7/2001 | Diab et al. | |
| 6,272,363 B1 | 8/2001 | Casciani et al. | |
| 6,272,367 B1 | 8/2001 | Chance | |
| 6,278,889 B1 | 8/2001 | Robinson | |
| 6,285,896 B1 | 9/2001 | Tobler et al. | |
| 6,304,767 B1 | 10/2001 | Soller et al. | |
| 6,353,226 B1 | 3/2002 | Khalil et al. | |
| 6,377,840 B1 | 4/2002 | Gritsenko et al. | |
| 6,377,841 B1 | 4/2002 | Lin et al. | |
| 6,381,018 B1 | 4/2002 | Bigio et al. | |
| 6,408,198 B1 | 6/2002 | Hanna et al. | |
| 6,411,832 B1 | 6/2002 | Guthermann | |
| 6,411,838 B1 | 6/2002 | Nordstrom et al. | |
| 6,421,549 B1 | 7/2002 | Jacques | |
| 6,434,408 B1 | 8/2002 | Heckel | |
| 6,438,397 B1 | 8/2002 | Bosquet et al. | |
| 6,438,399 B1 | 8/2002 | Kurth | |
| 6,456,862 B2 | 9/2002 | Benni | |
| 6,473,632 B1 | 10/2002 | Myers | |
| 6,480,276 B1 | 11/2002 | Jiang | |
| 6,498,942 B1 | 12/2002 | Esenaliev et al. | |
| 6,512,936 B1 | 1/2003 | Monfre et al. | |
| 6,516,209 B2 | 2/2003 | Cheng et al. | |
| 6,526,298 B1 | 2/2003 | Khalil et al. | |
| 6,549,284 B1 | 4/2003 | Boas et al. | |
| 6,564,088 B1 | 5/2003 | Soller et al. | |
| 6,567,165 B1 * | 5/2003 | Tsuchiya et al. | 356/338 |
| 6,575,965 B1 | 6/2003 | Fitch et al. | |
| 6,587,702 B1 | 7/2003 | Ruchti et al. | |
| 6,587,703 B2 * | 7/2003 | Cheng et al. | 600/310 |
| 6,594,518 B1 | 7/2003 | Benaron et al. | |
| 6,597,931 B1 | 7/2003 | Cheng et al. | |
| 6,615,061 B1 * | 9/2003 | Khalil et al. | 600/310 |
| 6,615,064 B1 | 9/2003 | Aldrich | |
| 6,615,065 B1 | 9/2003 | Barrett et al. | |
| 6,630,673 B2 | 10/2003 | Khalil et al. | |
| 6,635,491 B1 | 10/2003 | Khalil et al. | |
| 6,640,130 B1 | 10/2003 | Freeman et al. | |
| 6,647,280 B2 | 11/2003 | Bahr et al. | |
| 6,654,620 B2 | 11/2003 | Wu et al. | |
| 6,662,031 B1 | 12/2003 | Khalil et al. | |
| 6,662,033 B2 | 12/2003 | Casciani et al. | |
| 6,667,803 B1 | 12/2003 | Flessland et al. | |
| 6,678,541 B1 | 1/2004 | Durkin et al. | |
| 6,701,170 B2 | 3/2004 | Stetson | |
| 6,711,425 B1 | 3/2004 | Reuss | |
| 6,711,426 B2 | 3/2004 | Benaron et al. | |
| 6,714,805 B2 | 3/2004 | Jeon et al. | |
| 6,748,259 B1 | 6/2004 | Benaron et al. | |
| 6,801,316 B2 | 10/2004 | Guthermann | |
| 6,801,648 B2 | 10/2004 | Cheng | |
| 6,801,797 B2 | 10/2004 | Mannheimer et al. | |
| 6,801,799 B2 | 10/2004 | Mendelson | |
| 6,810,279 B2 | 10/2004 | Mansfield et al. | |
| 6,816,241 B2 | 11/2004 | Grubisic | |
| 6,836,502 B2 | 12/2004 | Canady et al. | |
| 6,845,256 B2 | 1/2005 | Chin et al. | |
| 6,898,451 B2 | 5/2005 | Wuori | |
| 6,934,570 B2 | 8/2005 | Kiani et al. | |
| 6,937,885 B1 | 8/2005 | Lewis et al. | |
| 6,957,094 B2 | 10/2005 | Chance et al. | |
| 6,968,222 B2 | 11/2005 | Burd et al. | |
| 6,985,763 B2 | 1/2006 | Boas et al. | |
| 6,990,364 B2 | 1/2006 | Ruchti et al. | |
| 6,992,775 B2 | 1/2006 | Soliz et al. | |
| 6,999,904 B2 | 2/2006 | Weber et al. | |
| 7,013,172 B2 | 3/2006 | Mansfield et al. | |
| 7,018,338 B2 | 3/2006 | Vetter et al. | |
| 7,027,849 B2 | 4/2006 | Al-Ali | |

| | | | |
|---|---|---|---|
| 7,039,446 B2 | 5/2006 | Ruchti et al. | |
| 7,039,538 B2 | 5/2006 | Baker, Jr. | |
| 7,047,054 B2 | 5/2006 | Benni | |
| 7,062,306 B2 | 6/2006 | Benaron et al. | |
| 7,068,867 B2 | 6/2006 | Adoram et al. | |
| 7,072,701 B2 | 7/2006 | Chen et al. | |
| 7,079,880 B2 | 7/2006 | Stetson | |
| 7,102,158 B2 | 9/2006 | Tysoe et al. | |
| 7,102,752 B2 | 9/2006 | Kaylor et al. | |
| 7,139,076 B1 | 11/2006 | Marbach | |
| 7,142,901 B2 | 11/2006 | Kiani et al. | |
| 7,147,153 B2 | 12/2006 | Rowe et al. | |
| 7,215,984 B2 | 5/2007 | Diab et al. | |
| 7,215,986 B2 | 5/2007 | Diab et al. | |
| 7,239,901 B2 | 7/2007 | Gritsenko | |
| 7,239,902 B2 | 7/2007 | Schmitt et al. | |
| 7,247,142 B1 | 7/2007 | Elmandjra et al. | |
| 7,274,955 B2 | 9/2007 | Kiani et al. | |
| 7,297,119 B2 | 11/2007 | Westbrook et al. | |
| 7,302,284 B2 | 11/2007 | Baker, Jr. et al. | |
| 7,304,724 B2 | 12/2007 | Durkin et al. | |
| 7,313,427 B2 | 12/2007 | Benni | |
| 7,315,752 B2 | 1/2008 | Kraemer et al. | |
| 7,315,753 B2 | 1/2008 | Baker, Jr. et al. | |
| D567,949 S | 4/2008 | Lash et al. | |
| 7,355,688 B2 | 4/2008 | Lash et al. | |
| D568,479 S | 5/2008 | Mao et al. | |
| 7,376,454 B2 | 5/2008 | Casciani et al. | |
| 7,427,165 B2 | 9/2008 | Benaron et al. | |
| 7,599,065 B2 * | 10/2009 | Sendai | 356/432 |
| 7,603,151 B2 | 10/2009 | Rebec et al. | |
| 7,623,956 B2 | 11/2009 | Kawaguchi | |
| 7,640,403 B2 | 12/2009 | Matsushima | |
| 2002/0033454 A1 | 3/2002 | Cheng et al. | |
| 2002/0035317 A1 | 3/2002 | Cheng et al. | |
| 2002/0065469 A1 | 5/2002 | Hsu | |
| 2003/0013973 A1 | 1/2003 | Georgakoudi et al. | |
| 2003/0065269 A1 | 4/2003 | Vetter et al. | |
| 2003/0212316 A1 | 11/2003 | Leiden et al. | |
| 2004/0010192 A1 | 1/2004 | Benaron et al. | |
| 2004/0039274 A1 | 2/2004 | Benaron et al. | |
| 2004/0058311 A1 | 3/2004 | Fletcher et al. | |
| 2004/0059210 A1 | 3/2004 | Stetson | |
| 2004/0114109 A1 | 6/2004 | Soliz et al. | |
| 2005/0058456 A1 | 3/2005 | Yoo | |
| 2005/0060336 A1 | 3/2005 | Abercrombie et al. | |
| 2005/0203357 A1 | 9/2005 | Debreczeny et al. | |
| 2005/0283052 A1 | 12/2005 | Al-Ali et al. | |
| 2005/1027781 | 12/2005 | Myers | |
| 2006/0004270 A1 | 1/2006 | Bedard et al. | |
| 2006/0009688 A1 | 1/2006 | Lamego et al. | |
| 2006/0018525 A1 | 1/2006 | Barbour | |
| 2006/0100489 A1 | 5/2006 | Pesach et al. | |
| 2006/0106293 A1 | 5/2006 | Fantini | |
| 2006/0111623 A1 | 5/2006 | Stetson | |
| 2006/0122475 A1 | 6/2006 | Balberg et al. | |
| 2006/0189861 A1 | 8/2006 | Chen et al. | |
| 2006/0195024 A1 | 8/2006 | Benni | |
| 2006/0200015 A1 | 9/2006 | Baker, Jr. | |
| 2006/0211922 A1 | 9/2006 | Al-Ali et al. | |
| 2006/0211932 A1 | 9/2006 | Al-Ali et al. | |
| 2006/0241363 A1 | 10/2006 | Al-Ali et al. | |
| 2006/0247514 A1 | 11/2006 | Panasyuk et al. | |
| 2006/0258928 A1 | 11/2006 | Ortner et al. | |
| 2007/0015981 A1 | 1/2007 | Benaron et al. | |
| 2007/0016079 A1 | 1/2007 | Freeman et al. | |
| 2007/0020181 A1 | 1/2007 | Workman et al. | |
| 2007/0051379 A1 | 3/2007 | Lash et al. | |
| 2007/0073124 A1 | 3/2007 | Li et al. | |
| 2007/0073128 A1 | 3/2007 | Hoarau et al. | |
| 2007/0093707 A1 | 4/2007 | Myers et al. | |
| 2007/0167694 A1 | 7/2007 | Causevic et al. | |
| 2007/0201788 A1 | 8/2007 | Liu et al. | |
| 2007/0203406 A1 | 8/2007 | Anderson et al. |
| 2007/0249913 A1 | 10/2007 | Freeman et al. |
| 2008/0004842 A1 | 1/2008 | Amelink et al. |
| 2008/0009689 A1 | 1/2008 | Benaron et al. |
| 2008/0009690 A1 | 1/2008 | Debreczeny et al. |
| 2008/0015424 A1 | 1/2008 | Bernreuter |
| 2008/0017800 A1 | 1/2008 | Benni |
| 2008/0097173 A1 | 4/2008 | Soyemi et al. |
| 2008/0106792 A1 | 5/2008 | Lash et al. |
| 2008/0108886 A1 | 5/2008 | Lash et al. |
| 2008/0188727 A1 | 8/2008 | Benaron et al. |
| 2008/0226137 A1 | 9/2008 | Benaron et al. |
| 2009/0137908 A1 | 5/2009 | Patwardhan |
| 2010/0152591 A1 | 6/2010 | Yu et al. |

OTHER PUBLICATIONS

Ali et al. "Spatially resolved spectroscopy (NIRO-300) does not agree with jugular bulb oxygen saturation in patients undergoing warm bypass surgery." 12$^{th}$ World Congress of Anaesthesiologists, Montreal, Canada, Jun. 4-9, 2000.

Barker et al. "Measurement of Carboxyhemoglobin and Methemoglobin by Pulse Oximetry: A Human Volunteer Study." Anesthesiology, vol. 105, No. 5; pp. 892-897; Nov. 2006.

Bartocci et al. "Pain activates cortical areas in the preterm newborn brain." International Association for the Study of Pain; vol. 122; pp. 109-117; 2006.

Bauer et al. "Impaired muscle oxygen use at onset of exercise in peripheral arterial disease." Journal of Vascular Surgery; vol. 40, No. 3; pp. 488-493; Sep. 2004.

Cheng et al. "Post-occlusive reactive hyperemia in patients with peripheral vascular disease." Clinical Hemorheology and Microcirculation; vol. 31; pp. 11-21; 2004.

Comerota et al. "Tissue (muscle) oxygen saturation (StO2): A new measure of symptomatic lower-extremity arterial disease." Journal of Vascular Surgery; vol. 38, No. 4; pp. 724-729; Oct. 2003.

Deeb et al. "Retrograde cerebral perfusion during hypothermic circulatory arrest reduces neurologic morbidity." Journal of Thoracic and Cardiovascular Surgery; vol. 109; pp. 259-268; 1995. (printout of website dated Nov. 20, 2008).

Doerschug et al. "Impairments in microvascular reactivity are related to organ failure in human sepsis." American Journal of Physiology—Heart and Circulatory Physiology; vol. 293; pp. H1065-H1071; 2007.

Fantini et al. "Non-invasive optical mapping of the piglet brain in real time." Optics Express; vol. 4, No. 8; pp. 308-314; Apr. 12, 1999.

Fantini et al. "Non-invasive optical monitoring of the newborn piglet brain using continuous-wave and frequency-domain spectroscopy." Physics in Medicine and Biology; vol. 44; pp. 1543-1563; 1999.

Gupta et al. "Measurement of brain tissue oxygenation performed using positron emission tomography scanning to validate a novel monitoring method." Journal of Neurosurgery; vol. 96; pp. 263-268; Feb. 2002.

Hemmerling, et al. "Significant decrease of cerebral oxygen saturation during single-lung ventilation measured using absolute oximetry." British Journal of Anaesthesia Advance Access; pp. 1-6; Oct. 3, 2008.

Hom et al. "Peripheral skin temperature effects on muscle oxygen levels." Journal of Thermal Biology; vol. 29; pp. 785-789; 2004.

Keller, B.P.J.A. "Risks and risk-analysis for the development of pressure ulcers in surgical patients." Thesis, University Utrecht; 2006.

Khaodhiar et al. "The Use of Medical Hyperspectral Technology to Evaluate Microcirculatory Changes in Diabetic Foot Ulcers and to Predict Clinical Outcomes." Diabetes Care; vol. 30, No. 4; pp. 903-910; Apr. 2007.

Koga et al. "Degree of Variation in Cerebral Tissue Oxyegnation Index (TOI) and Normalized Tissue Hemoglobin Index (NTHI) Measured by Near-Infrared Spectroscopy (NIRO-100)." Printout from website http://www.asaabstracts.com/strands/asaabstracts/printAbstract.htm;jsess..., Oct. 22, 2005.

Lee et al. "Use of T-Stat to predict colonic ischemia during and after endovascular aneurysm repair: A case report." Journal of Vascular Surgery; vol. 47, No. 3; pp. 632-634; Mar. 2008.

Masino Corporation. "Demystifying Methemoglobinemia: A Clinically Pervasive Disorder with Ambiguous Symptoms Masking Prevalence, Morbidity, and Mortality." Whitepaper from Masimo Corporation; 2006.

Maxim et al. "Optical Detection of Tumors in Vivo by Visible Light Tissue Oximetry." Technology in Cancer Research & Treatment; vol. 4, No. 3; pp. 227-234; Jun. 2005.

Nemoto et al. "Clinical experience with cerebral oximetry in stroke and cardiac arrest." Critical Care Medicine; vol. 28, No. 4; pp. 1052-1054; Apr. 2000. (printout of website dated Nov. 20, 2008).

Pollard et al. "Validation in Volunteers of a Near-Infrared Spectroscope for Monitoring Brain Oxygenation In Vivo." Anesthesia & Analgesia. vol. 82; pp. 269-277; 1996.

Rovati et al. "Optical and electrical recording of neural activity evoked by graded contrast visual stimulus." BioMedical Engineering OnLine; vol. 6, No. 28; Jul. 4, 2007.

Salvatori et al. "Instrumentation and calibration protocol for a continuous wave NIRS oximeter." Instrumentation and Measurement Technology Conference, Ottawa, Canada, May 17-19, 2005.

Strahovnik et al. "Measurement of skeletal muscle tissue oxygenation in the critically ill." Signa Vitae; vol. 3, No. 1; pp. 43-50; 2008.

Voga et al. "Improvement of Muscle Tissue Deoxygenation During Stagnant Ischemia in Survivors of Severe Sepsis." ESECM $17^{th}$ Annual Congress, Berlin, Germany, Oct. 10-13, 2004.

Xu et al. "Near Infrared Imaging of Tissue Heterogeneity: Probe Design and Sensitivity Analysis." 2005 IEEE Eneineering in Medicine and Biology $27^{th}$ Annual Conference, Shanghai, China, Sep. 1-4, 2005.

Yoshitani et al. "A Comparison of the INVOS 4100 and the NIRO 300 Near-Infrared Spectrophotometers." Anesthesia & Analgesia. vol. 94; pp. 586-590; 2002.

Yoshitani et al. "Effects of Hemoglobin Concentration, Skull Thickness, and the Area of the Cerebrospinal Fluid Layer on Near-infrared Spectroscopy Measurements." Anesthesioloty; vol. 106, No. 3; pp. 458-462; Mar. 2007.

Zonios et al. "Modeling diffuse reflectance from semi-infinite turbid media: application to the study of skin optical properties." Optics Express; vol. 14, No. 19; pp. 8661-8674; Sep. 18, 2006.

Johns et al. "Determination of Reduced Scattering Coefficient of Biological Tissue from a Needle-like Probe." Optics Express, vol. 13, No. 13, pp. 4828-4842; Jun. 27, 2005.

* cited by examiner

APPARATUS AND METHOD FOR DETERMINING ANALYTE CONCENTRATIONS

RELATED APPLICATIONS

This non-provisional patent application claims priority benefit with regard to all common subject matter of the earlier filed U.S. Provisional Patent Application titled "Method to Determine Coefficients and Scattering Analyte Concentrations", Ser. No. 61/331,645, filed on May 5, 2010, which is hereby incorporated by reference in its entirety into the present application.

BACKGROUND

1. Field

Embodiments of the present invention relate to a method and apparatus for determining scattering coefficients and analyte concentrations.

2. Related Art

Optical spectroscopy and spatially resolved measurements of light propagated through and/or reflected off of turbid media have been widely used to determine concentration of analytes, scattering coefficients, reduced scattering coefficients, and other physiologically relevant parameters in biological samples and tissues. These methods are typically based on measuring the propagation of light modulated by intrinsic optical properties of biological tissues and/or samples. Known optical properties of biological samples and tissues have been used to assess parameters related to metabolism, function of various tissues and organ systems, etc.

Spatially resolved diffuse spectroscopy is used to monitor clinical states of a patient or user by computing concentrations of analytes and scattering coefficients using spatially and spectrally resolved measurements of propagated light. Multivariate calibration techniques and diffusion model-based approaches are used to determine concentrations of analytes such as hemoglobin derivatives and other commonly observed analytes.

Non-uniqueness is a disadvantage of the measurement techniques mentioned above. That is, several sets of optical properties, such as several different scattering coefficients or reduced scattering coefficients, could correspond to numerically identical measurements of reflectance. At a certain range of emitter-detector separations (lateral distances between a light emitter and detector), at least two values of reduced scattering coefficients at a specified value of an absorption coefficient may correspond with numerically identical measurements of reflectance. These factors can result in large errors in quantification of analyte concentrations. One way of addressing this problem is to constrain scattering coefficients or reduced scattering coefficients to values available from published literature to determine concentrations from multiple wavelength reflectance or transmittance measurements.

Additionally, another disadvantage of the prior art methods is undesired cross-talk between absorption and scattering parameters, which has been demonstrated in a publication by Corlu et al. A. Corlu, T. Durduran, R. Choe, M. Schweiger, E M. C. Hillman, S. R. Arridge, and A. G. Yodh, entitled "Uniqueness and wavelength optimization in continuous-wave multispectral diffuse optical tomography," Opt. Lett. 28, 2339-2341 (2003).

Various prior art publications disclose analyzing reflectance and absorption of propagated light in determining analyte concentrations. Both reflectance and absorption are components of propagated light that take into account frequency and time components along with multipath interference and scattering factors, such as scattering coefficients. Scattering coefficients have largely been ignored or avoided in prior art methods.

Simple and complex calibration approaches have been developed to characterize tissues based on their scattering coefficient or absorption alone or some combination thereof. Additionally, modified diffusion theory and Monte-Carlo based expressions have also been developed and utilized for this purpose. Scattering coefficient and absorption related parameters such as hemoglobin derivatives and other analyte concentrations have been estimated using these methods. A limitation of these methods is that they are restricted to the UV-VIS region of the spectrum where the absorption of analytes is significantly large. The penetration depth at these wavelengths is very shallow when compared to wavelengths in the NIR regions (650-1000 nm). Another limitation of prior art methods using the diffusion model or diffusion theory is that this typically results in more unknowns than equations.

Accordingly, there is a need for a method and apparatus for determining analyte concentrations that overcomes the limitations of the prior art.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

Embodiments of the present invention solve the above-mentioned problems and provide a distinct advance in the art of measuring analyte concentrations. Specifically, the present invention provides an apparatus and method for quantifying optical properties and/or physiological parameters of biological samples, which include absorption and scattering coefficients or reduced scattering coefficients. One embodiment of the invention comprises a probe apparatus having one or more emitters delivering illumination at multiple wavelengths with at least one detector at close proximity to the emitter(s) and at least another detector further away from the emitter(s), laterally.

Various embodiments of the invention also comprise a method to quantify/characterize optical properties and concentrations of biological or diagnostic analyte based on the fraction of illuminated signal that is diffusively reflected by the tissue and measured by detectors placed as described earlier. The present invention may be a stand alone device and/or may be a part of a bigger system that may be used to characterize concentration of analytes, reduced scattering coefficients, scattering coefficients, or physiological parameters of samples.

BRIEF DESCRIPTION OF THE DRAWING FIGURES

Embodiments of the present invention are described in detail below with reference to the attached drawing figures, wherein.

Figure 3:
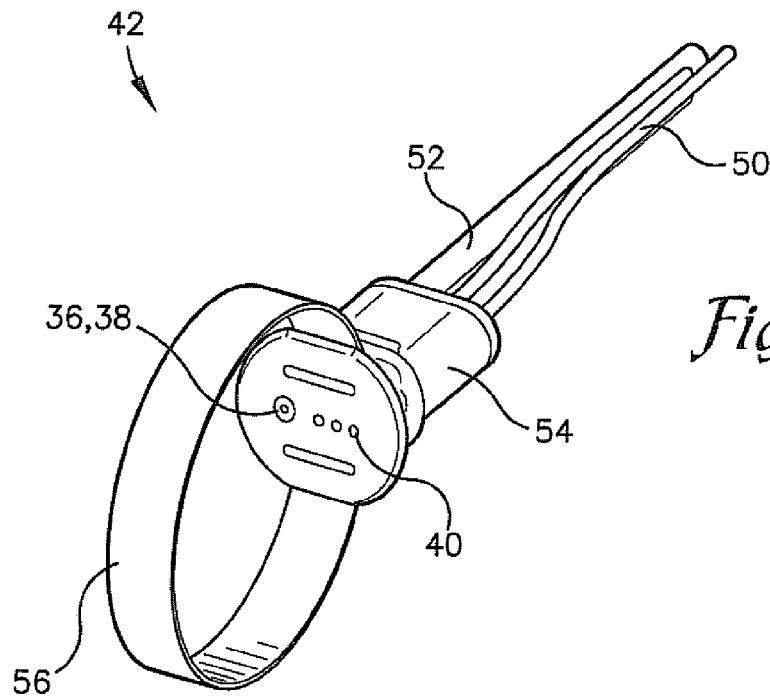
FIG. 3 is a perspective view of a measuring head of the system of FIG. 1, configured for measurement of analyte concentrations and scattering coefficients and constructed in accordance with an embodiment of the present invention.
Figure 14:
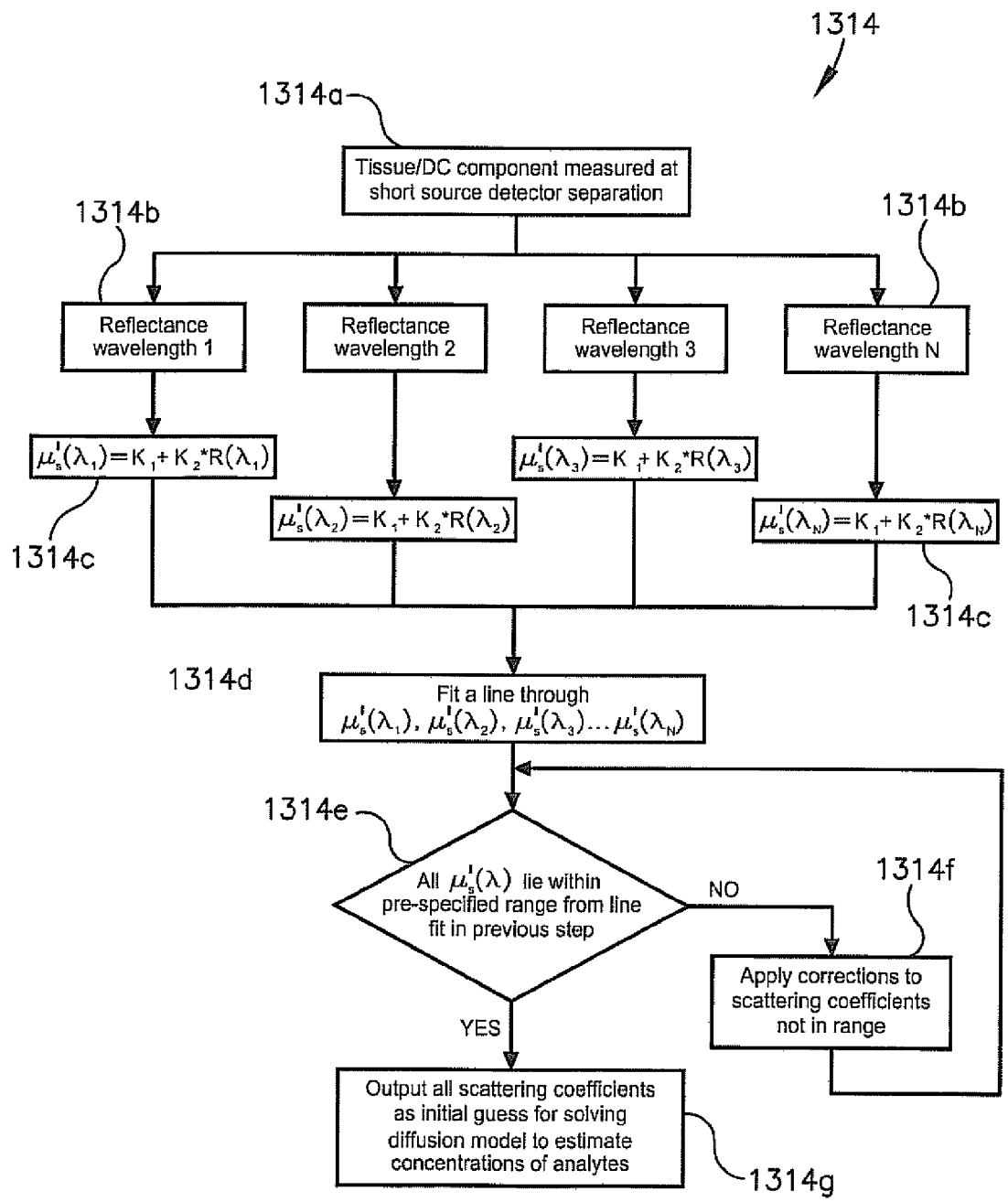
FIG. 14 is a flow chart illustrating a method of determining scattering coefficients or reduced scattering coefficients with reflectance measurements from a short emitter-detector separation distance, as in step 1314 of FIG. 13.
Figure 15:
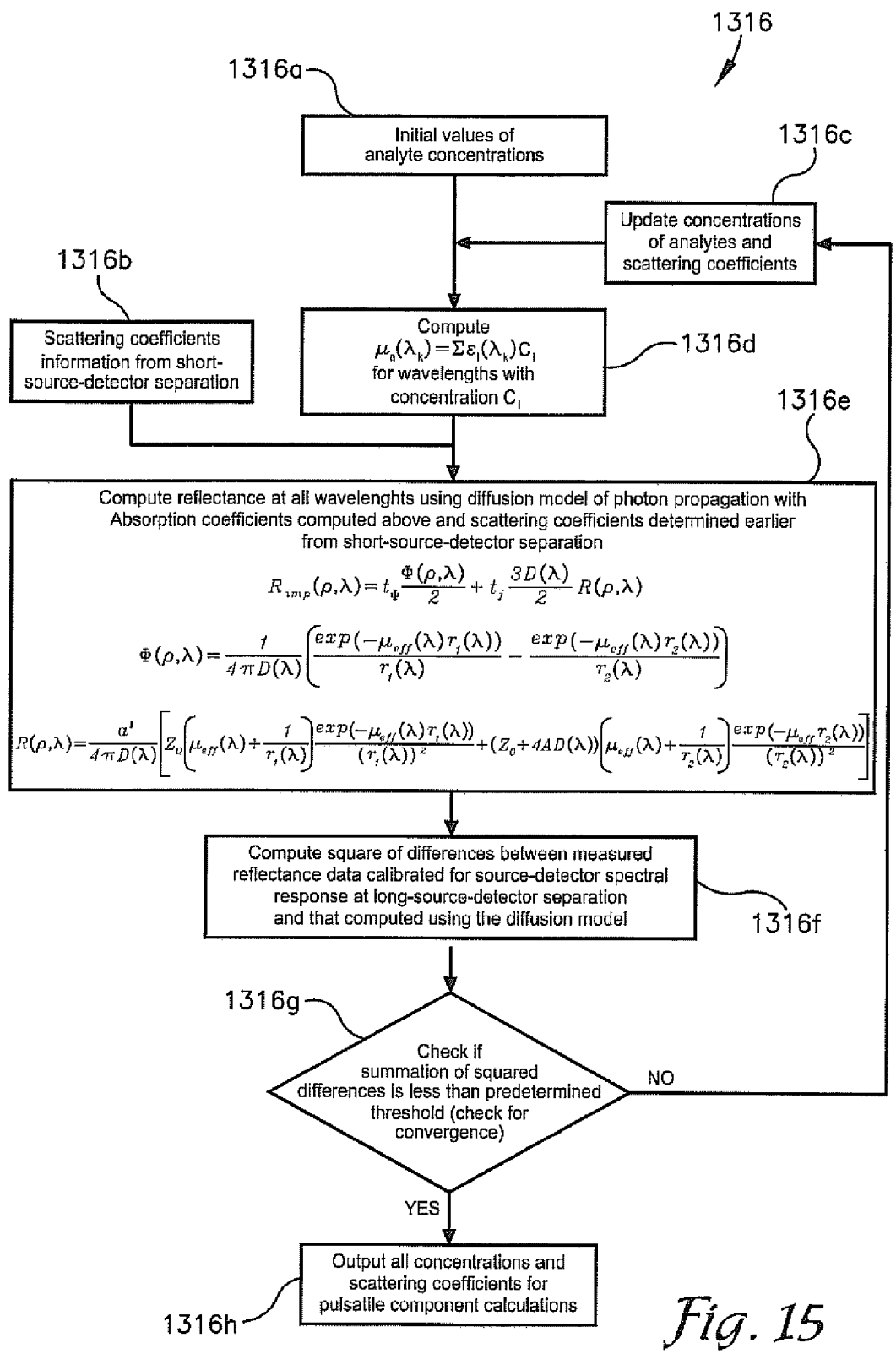
Figure 16:
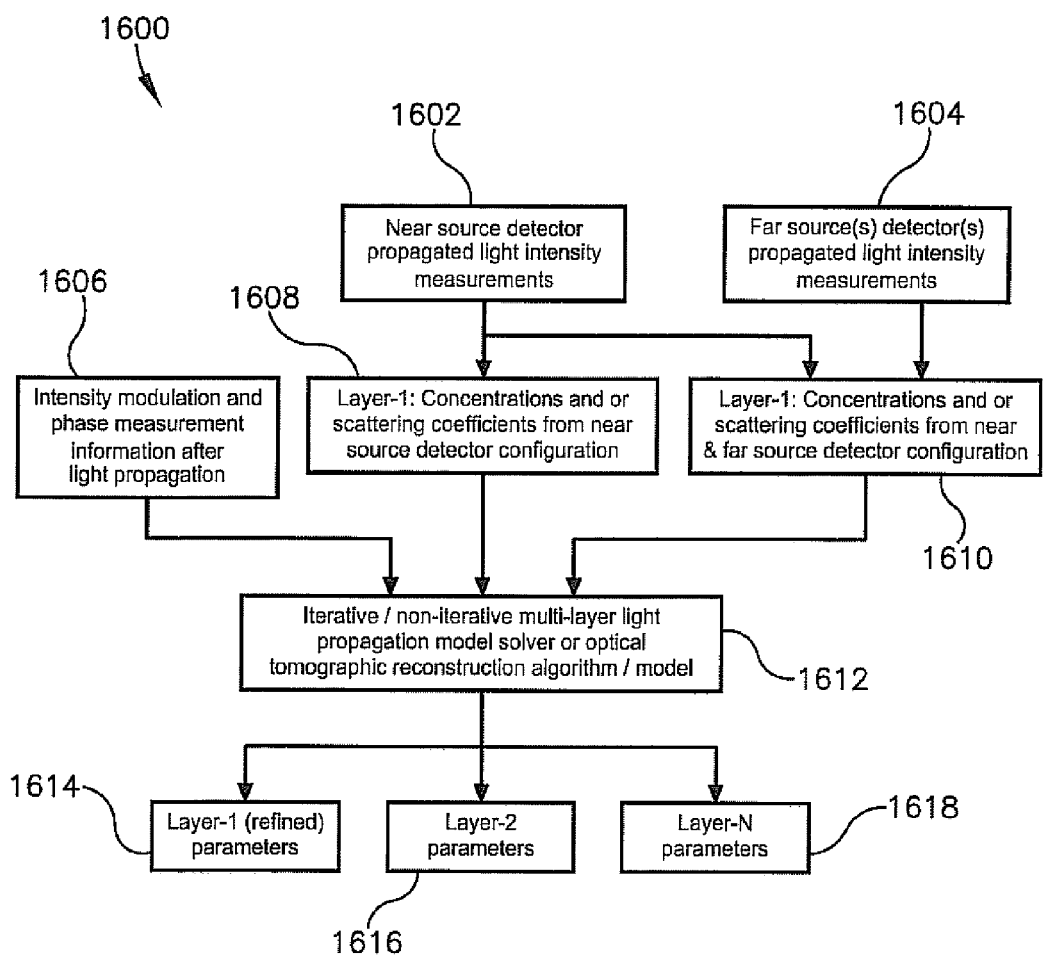

FIG. 15 is a flow chart illustrating a method of calculating analyte concentrations using the scattering coefficients or reduced scattering coefficients determined in step 1314 and absorption coefficients calculated with reflectance determined from a long emitter-detector separation distance, as in step 1316 of FIG. 14; and FIG. 16 is a flow chart illustrating an exemplary use of measurements obtained by the measuring head of FIG. 3 in conjunction with frequency or time domain systems.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
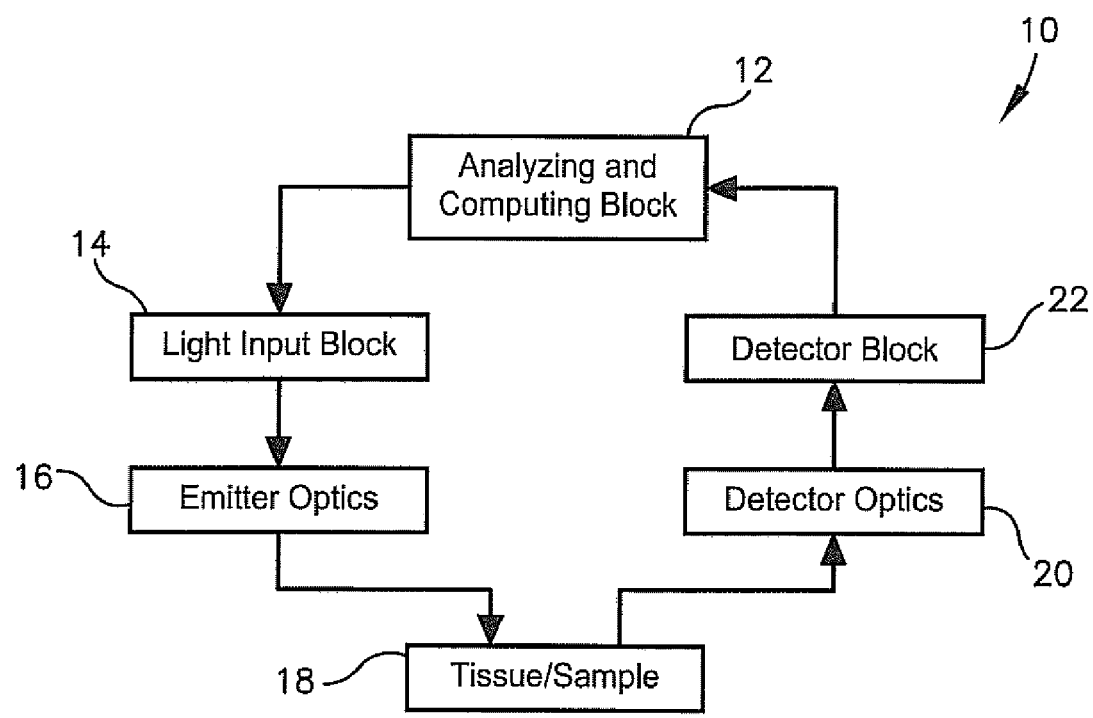
FIG. 1 is a block diagram of an analyte concentration measurement system constructed in accordance with an embodiment of the present invention.

One embodiment, illustrated in FIG. 1, is generally related to an apparatus and method for determining optical properties and/or physiological parameters of tissues and other biological samples. Specifically, the embodiment uses a probe apparatus 10 and method to determine concentrations of biological or diagnostic analytes, absorption coefficients, scattering coefficients, and/or reduced scattering coefficients of tissues.

A block diagram of the probe apparatus 10 for the determination of concentrations of analytes and scattering properties is illustrated in FIG. 1. The probe apparatus 10 consists of an analyzing and computing block 12, a light source block 14, an emitter optics block 16 delivering light to a tissue sample 18, a detector optics block 20 collecting propagated light from the sample or tissue, and a detector block 22. The emitter and detector optics 16,20 may be integrated into a measuring head 42 or probe, as illustrated in FIG. 3. The measuring head 42 or probe may be placed in contact with a surface of the biological tissue or test sample 18, or may be invasively introduced into the body or a sample.

Figure 2:
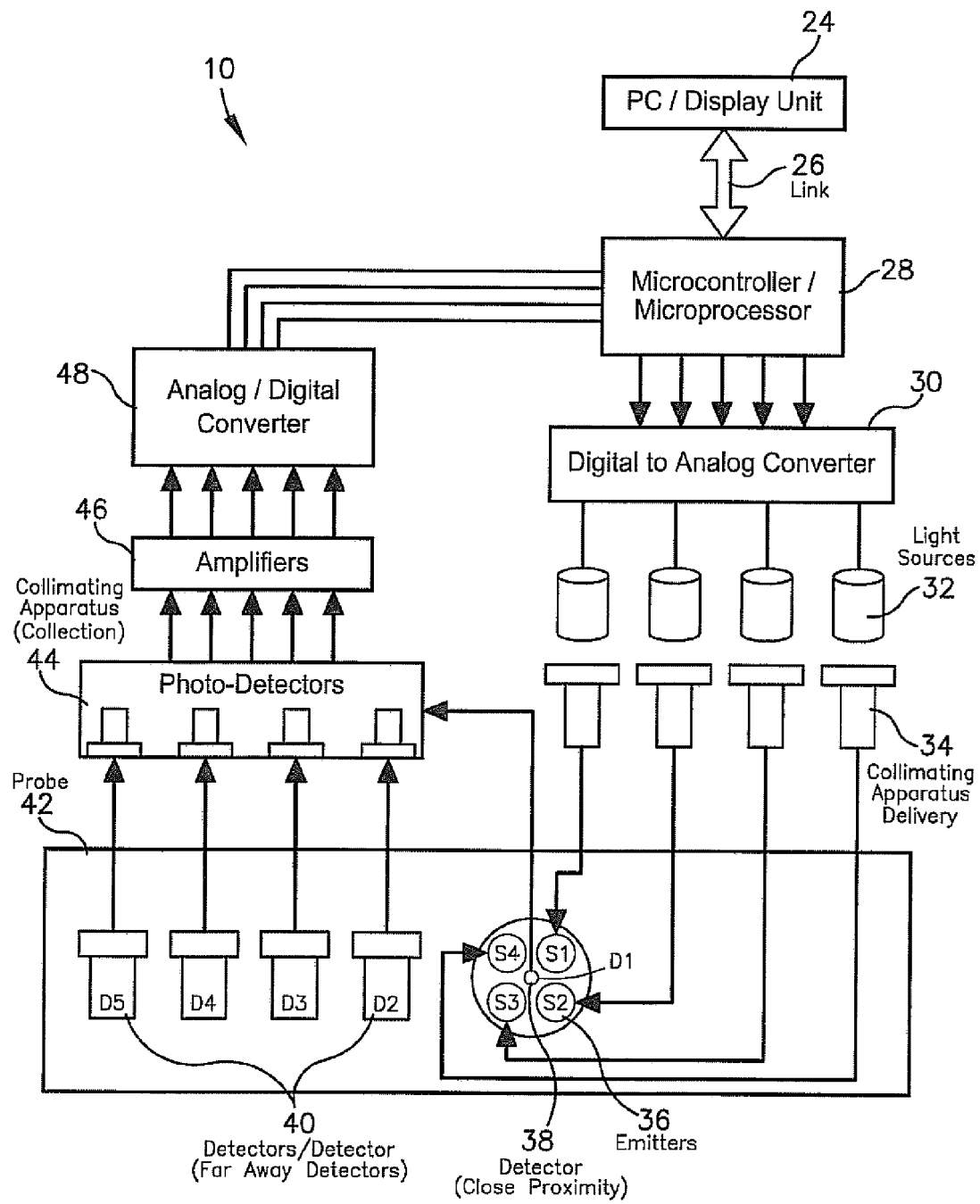
FIG. 2 is a schematic drawing of a probe apparatus, with optical fibers for transmitting light, constructed in accordance with an embodiment of the present invention.

The measuring head 42 of the probe apparatus 10 may contain at least one emitter 36 as a light irradiating source and at least two detectors 38,40, as illustrated in FIG. 2. At least one of these detectors 38 may be placed in close lateral proximity to the emitter 36. At least one detector 40 may be placed further away, laterally, from the emitter 36.

FIG. 2 illustrates an embodiment of the invention which comprises one detector 38 (labeled D1) placed in close lateral proximity (e.g., approximately less than 2 mm, or preferably less than 1.3 mm) to the emitters 36 (labeled S1-S4) and four detectors 40 (labeled D2-D5) placed further away, laterally, from the emitters 36 (e.g., approximately greater than 0.5 cm, greater than 0.7 cm, or greater than 1.0 cm). Lateral distance as defined herein may also refer to radial distance. In this embodiment, light sources are located away from the sample. Light from the sources may be delivered to the emitters through optical fibers, as later described herein. In an example embodiment of the invention, the wavelengths of the light sources may be 660 nm for S1, 810 nm for S2, 910 nm for S3, and 1310 nm or 980 nm for S4.

In various embodiments of the invention, light sources 14,32 may be either LEDs, laser diodes, or sources of suitable wavelengths in the wavelength range of approximately 500-1350 nm. Note that the wavelength range provided herein is merely an example and should not be considered to restrict the scope of the invention. The specific wavelength range employed will depend on the set of analytes to be characterized or measured and the nature of the media in which the analytes or chromophores are present.

The required power output of the light sources 14,32 may be based on a base line level of analyte concentrations and maximum lateral distances between emitters 16,36 and detectors 20,38,40. Pulsed or intensity-modulated light sources may be used to reduce energy dissipation from the light-irradiating sources. Alternatively, a white light source with notch filters at required wavelengths may be used. Optical filter wheels or tunable optical filters may also be used to deliver illumination at required wavelengths. Additionally, a light collimation apparatus 34 comprising at least one converging lens may be used to increase efficiency of light coupling between sources and transmitting optical fibers.

Digital-to-Analog converters (DAC) 30 of requisite accuracy may be used to drive the illuminating light sources 32. Control signals for the switching of the DAC may be generated in analyzing and processing units later described herein.

In the probe apparatus 10 demonstrated in the embodiment in FIG. 2, detector D1 (close proximity detector 38), detects reflectance from the sample 18 surface at a close proximity to the light emitter 36, and detectors D2, D3, D4 & D5 (far away detectors 40) are located further away from emitters 36 to detect reflected light. In the embodiment of the invention illustrated in FIG. 2, reflected light received by the detectors 38,40 is transmitted from a surface of the sample 18 to one or more photo detectors 44 through optical fibers.

The photo detectors 44 may be photo-diodes, CCD-Detectors, CMOS sensors, and Photon Multiplier Tubes (PMT) and/or may comprise a light collimating apparatus. Additionally, the light collimation apparatus may comprise at least one converging lens which may be used to increase efficiency of light coupling between photo detectors and transmitting optical fibers. The optical fibers or light received by each of the optical fibers may be detected individually and simultaneously by multiple photo detectors or detected one at a time using a switch (not shown) and at least one photo detector, or alternately using any combination of above approaches, as known in the art. For example, the switch may be an optical switch which selects light from one fiber at a time or a rotating shutter configured to select light from each optical fiber one at a time, allowing light received by each optical fiber to be individually detected by a detector or photodiode.

Elimination of interference from ambient sources of light can be accomplished using pulsed or frequency-selective techniques. It will be appreciated by those skilled in the art that several alternate forms of this embodiment might be used to accomplish this task. Any of these alternate forms may be used. One such specific example may include use of one photo detector and use of a filtering means to differentiate a plurality of wavelengths. As illustrated earlier, several variations of filtering means may be utilized to achieve the various objectives described herein.

An output signal from the photo-detectors 44 may be amplified by a suitable amplifier 46 and/or passed through an analog/digital converter 48. Then the output signal may be transmitted to a processing and analyzing unit 28, such as a computer, microcontroller, or microprocessor, to process acquired reflectance data and/or display computed results. This unit 28 may also be used to control the switching of light sources. In some embodiments of the invention, the unit 28 may comprise circuits that operate outside of traditional digital techniques to operate in the frequency domain. For example, a surface acoustic wave (SAW) filter may be used for doing real-time conversion into and out of the frequency domain.

Specifically, the unit 28 may include any number of processors, controllers, integrated circuits, programmable logic devices, or other computing devices and resident or external memory for storing data and other information accessed and/or generated by the probe apparatus 10. The methods described herein may be at least partially implemented on the unit 28. The unit 28 may be part of the analyzing and computing block 12 illustrated in FIG. 1 and may be coupled with the light source 14, emitters 16,36, detectors 20,22,38,40, a memory (not shown), at least one display (not shown), a user interface (not shown), and the other components through wired or wireless connections to enable information to be exchanged between the various components.

The unit 28 may implement a computer program and/or code segments to perform the functions and method described herein. The computer program may comprise an ordered listing of executable instructions for implementing logical functions in the unit 28. The computer program can be embodied in any computer readable medium for use by or in connection with an instruction execution system, apparatus, or device, and execute the instructions. In the context of this application, a "computer readable medium" can be any apparatus that can contain, store, communicate, propagate, or transport the program for use by or in connection with the instruction execution system, apparatus, or device. The computer readable medium can be, for example, but not limited to, an electronic, magnetic, optical, electro magnetic, infrared, or semi conductor system, apparatus, or device. More specific, although not inclusive, examples of the computer readable medium would include the following: a portable computer diskette, a random access memory (RAM), a read only memory (ROM), an erasable, programmable, read only memory (EPROM or flash memory), and a portable compact disk read only memory (CDROM).

The memory may be integral with the unit 28, stand alone memory, or a combination of both. The memory may include, for example, removable and non removable memory elements such as RAM, ROM, flash, magnetic, optical, USB memory devices, and/or other conventional memory elements.

The memory may store various data associated with the operation of the probe apparatus 10, such as the computer program and code segments mentioned above, or other data for instructing the unit 28 and other probe apparatus elements to perform the steps described herein. Furthermore, the memory may store, for example, known analyte concentrations, calibration information, etc. The various data stored within the memory may also be associated within one or more databases to facilitate retrieval of the information.

The display may comprise conventional black and white, monochrome, or color display elements including CRT, TFT, LCD, and/or LED display devices. The display may be integrated with the user interface, such as in embodiments where the display is a touch screen display to enable the user to interact with it by touching or pointing at display areas to provide information to the probe apparatus 10. The display may be coupled with the unit 28 and may be operable to display various information corresponding to the probe apparatus 10, such as data from the detectors 20,38,40 as described below. For example, the display may indicate calculated scattering coefficients, analyte concentrations, and/or other parameters determined based on information output by the detectors 20,38,40. However, the display may or may not be present in any embodiment of the invention without departing from the scope of the invention.

The user interface enables users to share information with the probe apparatus 10. The user interface may comprise one or more functionable inputs such as buttons, switches, scroll wheels, a touch screen associated with the display, voice recognition elements such as a microphone, pointing devices such as mice, touchpads, tracking balls, styluses, a camera such as a digital or film still or video camera, combinations thereof, etc. Further, the user interface may comprise wired or wireless data transfer elements such as a removable memory including the memory, data transceivers, etc., to enable the user and other devices or parties to remotely interface with the probe apparatus 10. The user interface may also include a speaker for providing audible instructions and feedback.

The programs or software may reside either on a microprocessor on-board or alternatively in a user program on any capable external computer 24. The external computer 24 may comprise a display, user interface, memory elements, etc., as described above for unit 28, and may be communicably coupled to the unit 28 wirelessly and/or via a communications link 26. In some embodiments, the computer 24 and the unit 28 may be a single integrated device or two separate devices located remotely from each other. In some embodiments, the unit 28 and the external computer 24 may cooperatively perform the method steps described herein.

In some embodiments, the probe apparatus 10 may also comprise Analog-to-Digital Converters (ADC) 48 to couple signals from photo detectors 44 to analyzing and processing units 28. Band pass filters may be utilized to band limit noise and improve the SNR of acquired signals. Alternatively, data acquisition boards with capability of on-board clocks, data buffering, high-speed data transfer, configurable and controllable by user programs can be used.

FIG. 3 demonstrates one example of the measuring head 42, including optical fibers 50,52 used to transmit light from light sources 14 to the sample 18 and deliver collected reflected light from the sample 18 to the detector optics 20, such as photo detectors. A strap 56 may be provided to hold the measuring head 42 in position. The emitters 36 and detector 38 at close proximity may be part of a single fiber bundle encased in a protective sheath. Detectors 40 further away from the emitters 36 may be held separately from the emitter's fiber bundle. A protective enclosure 54 may serve to hold all the fiber bundles 50,52 in place as well as prevent the breakage of fibers.

Figure 4:
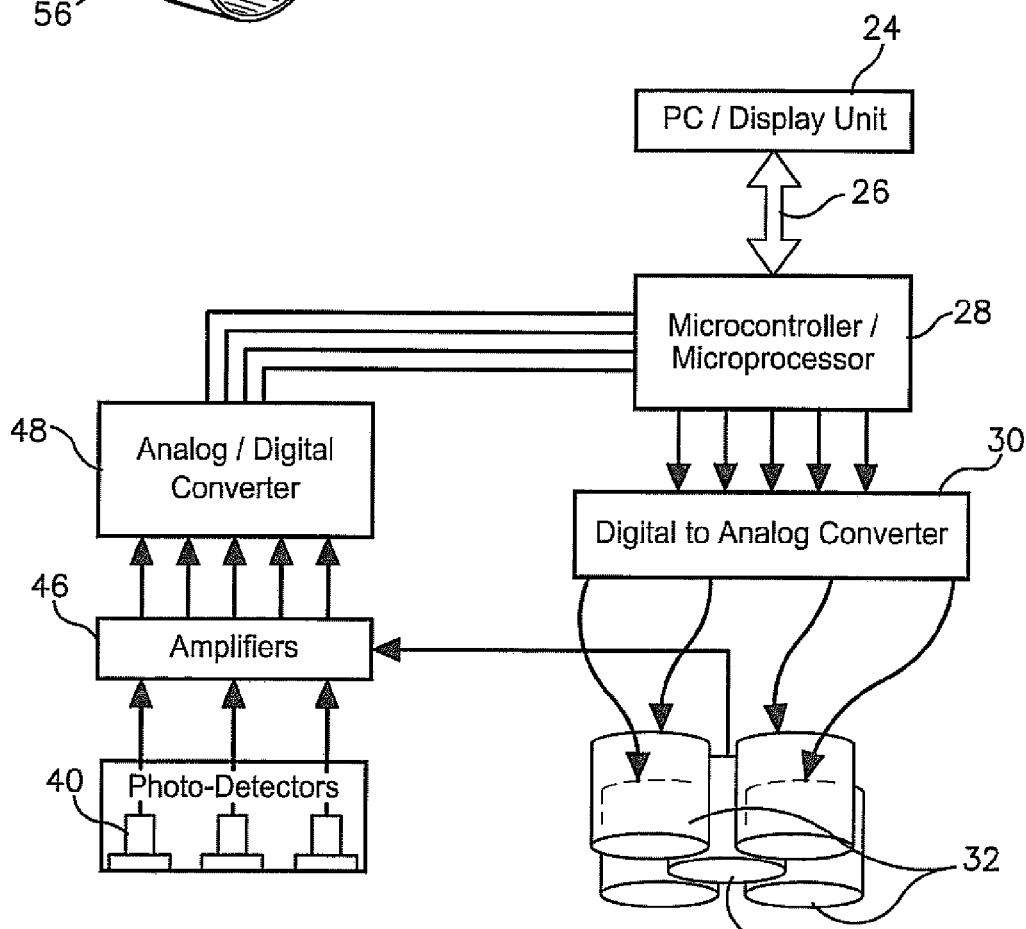
FIG. 4 is a schematic drawing of the probe apparatus of FIG. 2, with light sources and detectors configured to be placed in direct contact with a sample.

In an alternative embodiment, as illustrated in FIG. 4, light sources and detectors, together with necessary optics, are placed in direct contact with the sample, eliminating the need for light transmitting fibers. For example, the embodiment illustrated in FIG. 4 is similar to FIG. 2, except that light sources 32 are located on the measuring head 42 emitting light into the sample or tissue, eliminating the requirement for transmitting fibers. Also, in the embodiment illustrated in FIG. 4, the detectors 38,40 themselves are placed in contact with the tissue or sample, eliminating the requirement for light transmitting fibers.

Details of alternative designs and different configurations of emitters and detectors are illustrated in FIGS. 5-9. Specifically, irradiation means and detection means may be integrated into the probe apparatus 10 and additionally different configurations similar in principle to those demonstrated in FIGS. 1-4 may be used. Use of optical fibers may be particularly advantageous, due to their inherent compactness, light delivery and transport characteristics.

In configurations illustrated in FIGS. 5-9, as mentioned before, light sources may be placed in contact with sample or tissue as emitters or light from light sources may be delivered through optical fibers acting as emitters. Similarly, photo detectors may be placed in contact with the sample or light reflected from the sample or tissue surface may be delivered to photo detectors through optical fibers acting as detectors.

Figure 5:
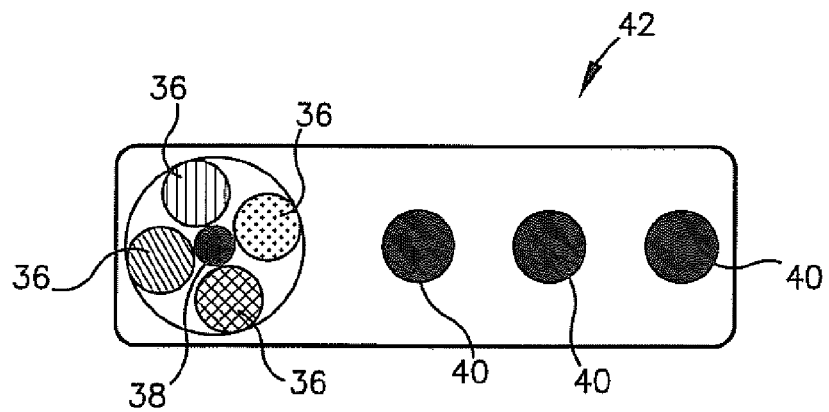
FIG. 5 is a schematic drawing of emitters and detectors of the measuring head of FIG. 3, arranged according to one embodiments of the invention.

FIG. 5 illustrates a measuring apparatus in accordance with one embodiment. The apparatus includes multiple emitters 36 (S1-S4) for radiating light towards the biological tissue or sample 18 placed around the close proximity detector 38 (D1) or a set of close proximity detectors for receiving light reflected back from the tissue or sample 18. This embodiment of the invention may also include the far-away detector(s) 40 spaced at least 1 cm away from emitters 36 (S1-S4) to collect the light emerging from the tissue sample 18. The far away detectors 40 may be linearly arranged, as in FIG. 5.

Figure 6:
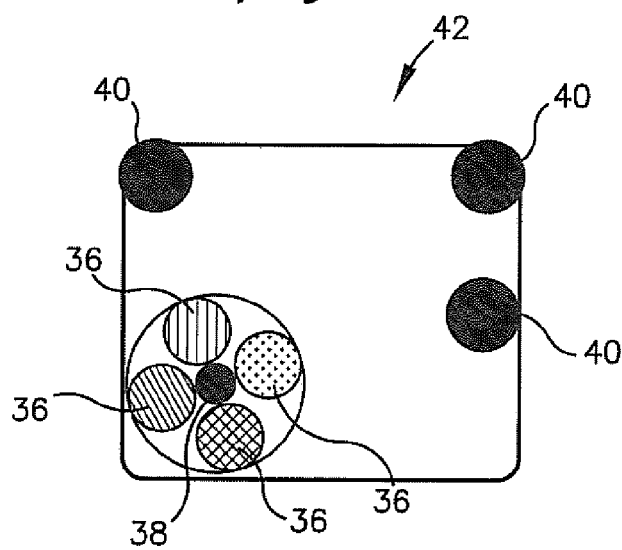
FIG. 6 is a schematic drawing of the emitters and detectors of the measuring head of FIG. 3, arranged according to an alternative embodiment of the invention.

Another alternative embodiment of the invention is illustrated in FIG. 6. The arrangement is not linear, but rather forms a rectangle, as shown. The length of the diagonal of the rectangle depicted in FIG. 6 can extended up to 2 cm, although larger or smaller distances may be used. Other dimensions may be scaled accordingly depending on the diagonal distances between the emitters 36 and detectors 38,40. Other detectors in this configuration may be placed as depicted or suitable variations that do not deviate from the basic principle of this embodiment may be utilized.

Figure 7:
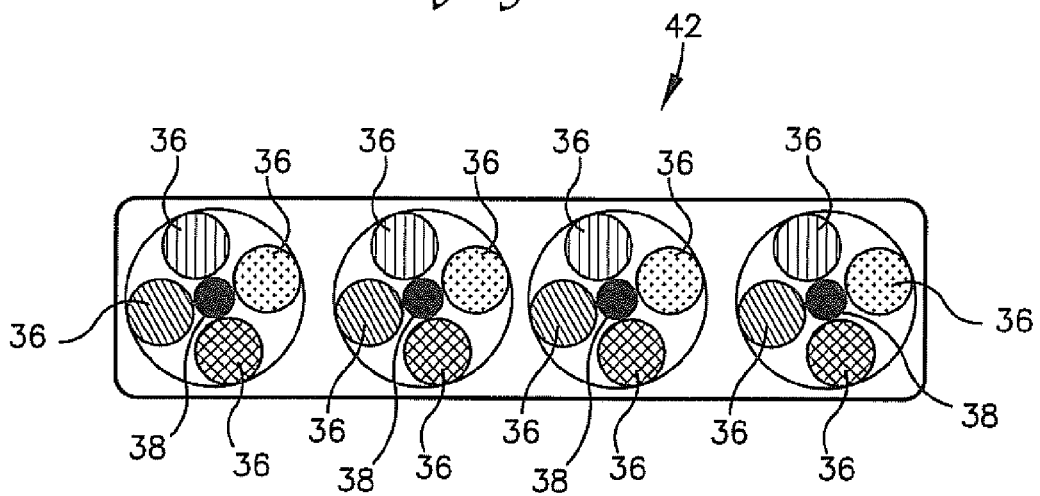
FIG. 7 is a schematic drawing of the emitters and detectors of the measuring head of FIG. 3, arranged according to another alternative embodiment of the invention.
Figure 8:
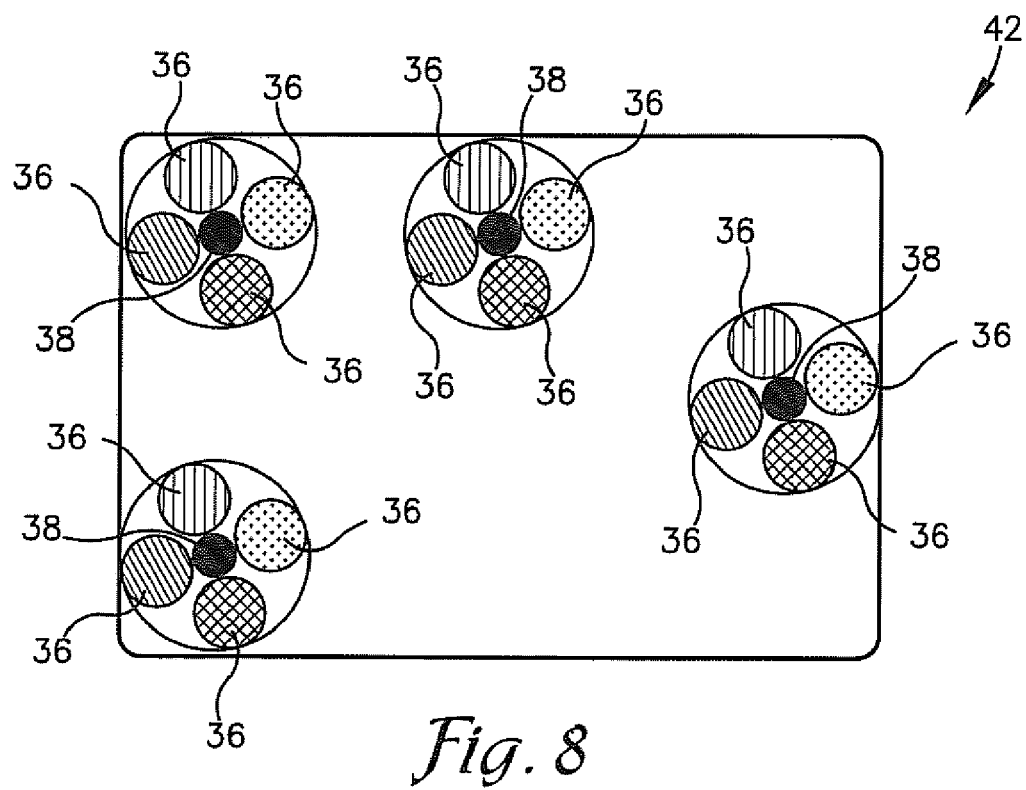
FIG. 8 is a schematic drawing of the emitters and detectors of the measuring head of FIG. 3, arranged according to yet another alternative embodiment of the invention.

FIGS. 7 and 8 demonstrate two alternative configurations of emitters and detectors. It is obvious that these configurations are similar to FIGS. 5 and 6 in that the arrangement of emitters 36 around detector 38 is repeated for each of the detectors 38. These configurations provide an added advantage of estimating reduced scattering coefficients or scattering coefficients (via a plurality of close proximity detectors 38) at spatially diverse locations, making measurements more accurate. Specifically, each of the detectors 38 illustrated in FIGS. 7 and 8 may function as both close proximity detectors 38 and far-away detectors 40. A simple or weighted average of determined scattering coefficients or reduced scattering coefficients may be used to determine analytical calculations. Reciprocal determinations may be used to increase accuracy of determined parameters. The configurations illustrated in FIGS. 7 and 8 may additionally provide means to determine topographic and tomographic maps of analyte concentrations and optical properties.

In some embodiments of the invention, multiple close proximity detectors 38 are used to allow a plurality of scattering coefficients or reduced scattering coefficients from spatially-diverse locations to be averaged, increasing accuracy. However, in these embodiments, the emitter-detector lateral separation distances between the emitter 36 and each of the close proximity detectors 38 may be identical or approximately identical. This avoids differences in scattering coefficient measurements or reduced scattering coefficient measurements caused by different detection distances. Note that measuring scattering coefficients or reduced scattering coefficients at a single separation distance eliminates differences in scattering coefficients or reduced scattering coefficients due to different investigated volumes or different detection distances.

Figure 9:
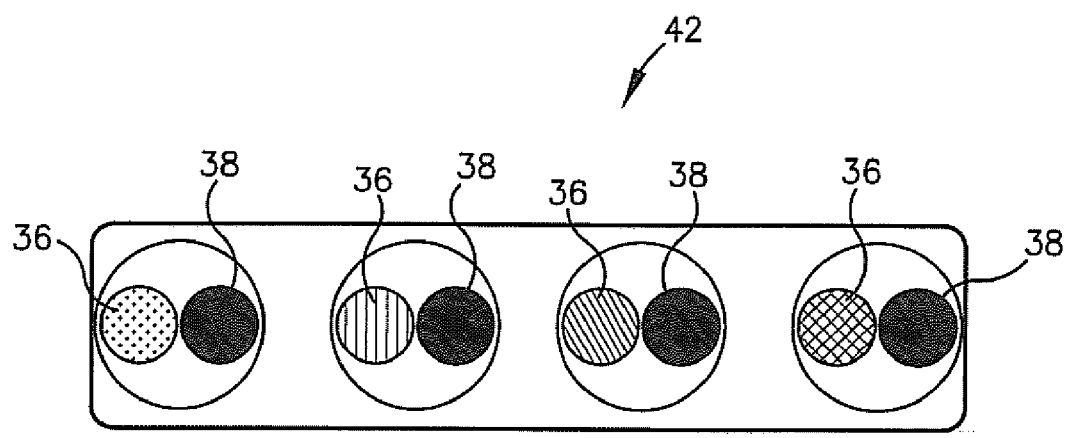
FIG. 9 is a schematic drawing of the emitters and detectors of the measuring head of FIG. 3, arranged in pairs according to an alternative embodiment of the invention.

FIG. 9 demonstrates an exemplary alternative embodiment of the optical probe apparatus 10. This configuration is suitable for white light sources. Emitters and detectors may be co-located on each optical fiber probe area. In this embodiment, there is only one emitter and one detector per group. Center-to-center lateral distances between the co-located emitter-detectors may be restricted to approximately 2 mm, or may be less than 1.3 mm. For example, the lateral distances between the co-located emitter-detectors may be approximately 1 mm. The core fiber sizes may vary depending on the incident power desired and maximum lateral distances used. This configuration may be suitable where white-light sources with or without filters are used as source of illuminations. It may also be suitable if the light detection means comprise spectrometers, CCD arrays, or spectrographs. Optics such as beam combiners may be used at the source end to combine light from sources of multiple wavelengths into one emitter. Frequency selective means or other means may be employed to differentiate and measure reflected light at a plurality of wavelengths.

A significant improvement of the present invention compared with previously known systems having multiple emitters and detectors at a plurality of distances from light emitters consists of locating detectors 38,40 at very close proximity away from the emitters 36 and at distances further away from the emitters 36, as illustrated in FIGS. 1-9. In some embodiments of the invention, the close proximity detectors 38 may be less than about 2 mm away from the emitters 36, less than about 1.3 mm away from the emitters 36, or preferably equal to or less than about 1.2 mm away from the emitters 36. For example, the close proximity detectors 38 may be about 1 mm away from the emitters 36. Furthermore, in some embodiments of the invention, the far away detectors 40 may be greater than about 0.5 cm away from the emitters 36, greater than 0.7 cm away from the emitters 36, greater than 0.8 cm away from the emitters 36, or greater than 1.0 cm away from the emitters 36. For example, the far away detectors 40 may be approximately 0.8 cm to 3 cm away from the emitters 36. The primary reasons for such an implementation are elaborated with the help of Monte Carlo simulations and substantiated through laboratory measurements on tissue phantoms.

Figure 10:
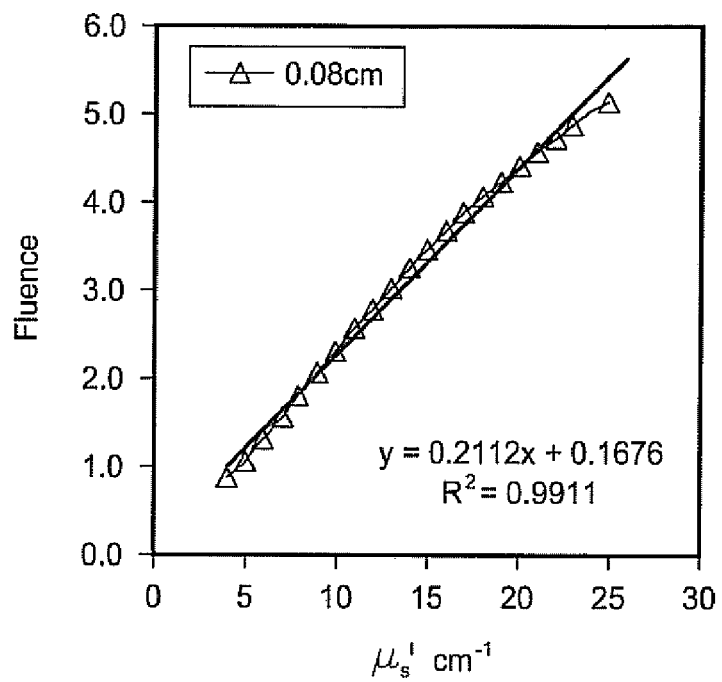
FIG. 10 is a graph of fluence versus reduced scattering coefficients measured with a detector spaced at a lateral distance of approximately 1 mm from the emitter.
Figure 11:
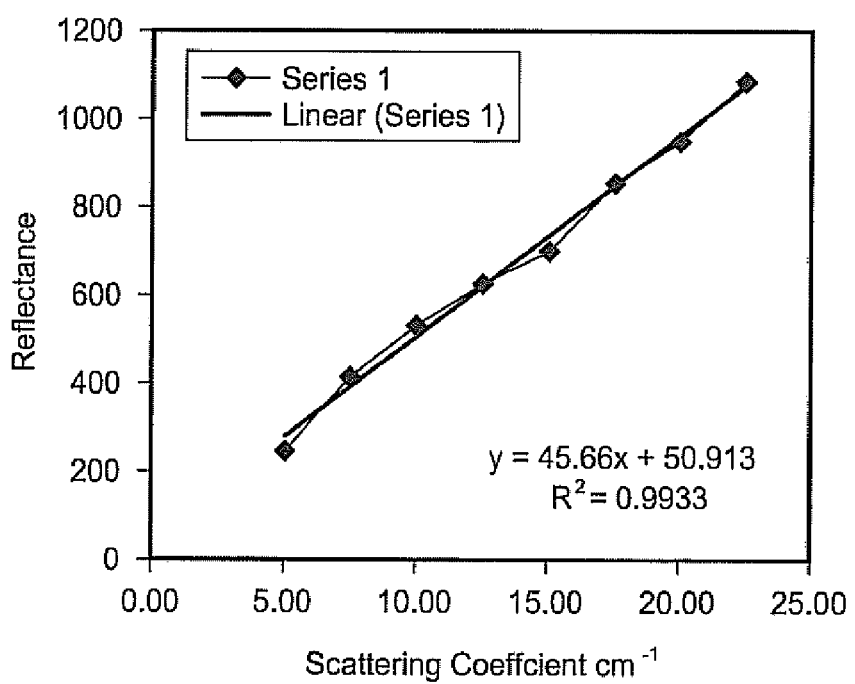
FIG. 11 is a graph of reflectance versus scattering coefficients measured with a detector spaced at a lateral distance of approximately 1 mm from the emitter.
Figure 12A:
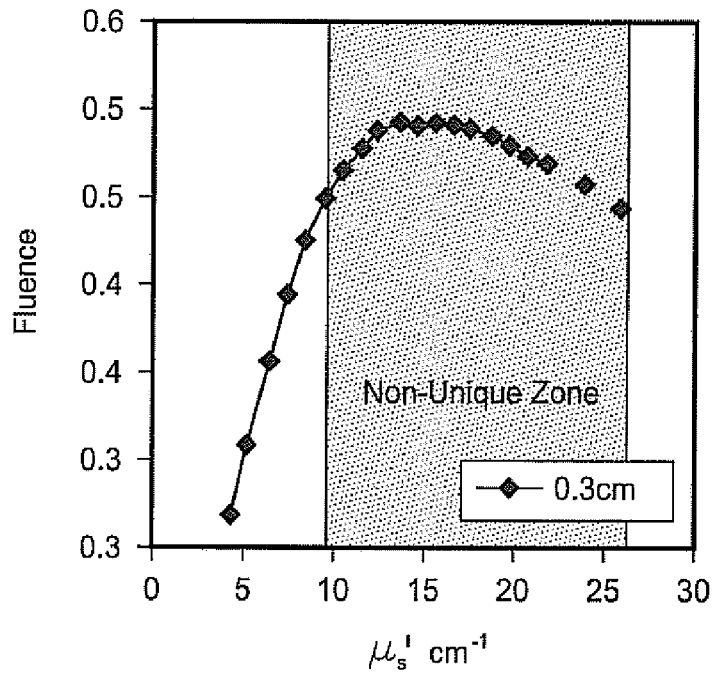
FIG. 12a is a graph of intensity values (reflectance and/or fluence) versus reduced scattering coefficients at detectors spaced 0.3 cm laterally from the emitter, demonstrating the non-monotonic dependence of reflectance (fluence) with reduced scattering coefficients at this lateral emitter-detector separation.
Figure 12B:
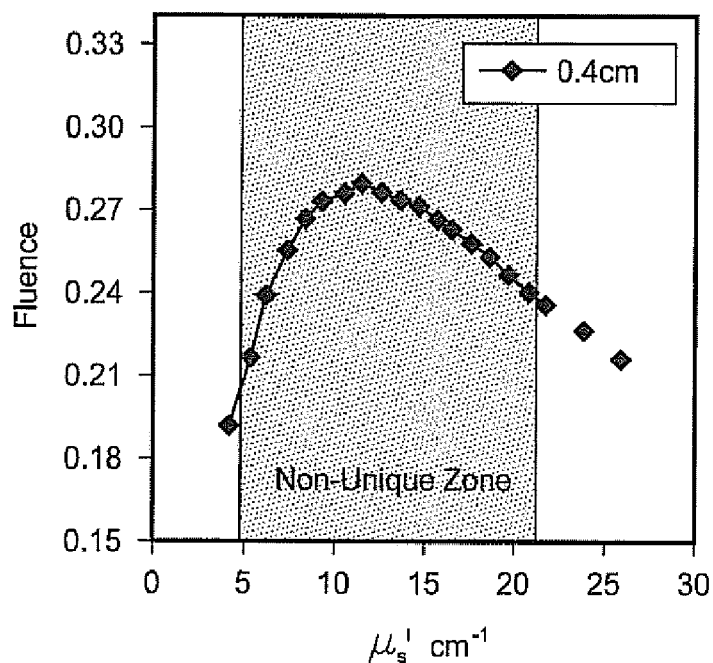
FIG. 12b is a graph of intensity values (reflectance and/or fluence) versus reduced scattering coefficients at detectors spaced 0.4 cm laterally from the emitter, demonstrating the non-monotonic dependence of reflectance (fluence) with reduced scattering coefficients at this lateral emitter-detector separation.
Figure 12C:
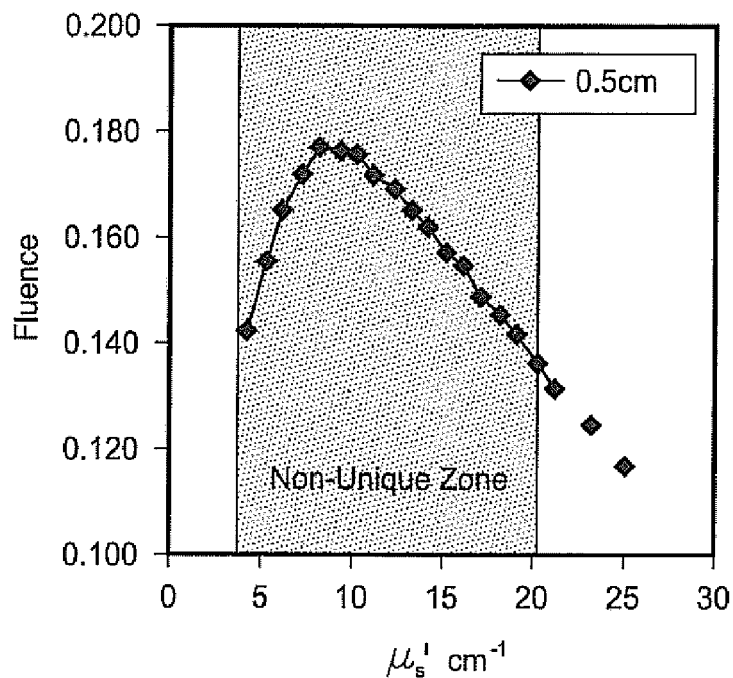
FIG. 12c is a graph of intensity values (reflectance and/or fluence) versus reduced scattering coefficients at detectors spaced 0.5 cm laterally from the emitter, demonstrating the non-monotonic dependence of reflectance (fluence) with reduced scattering coefficients at this lateral emitter-detector separation.
Figure 12D:
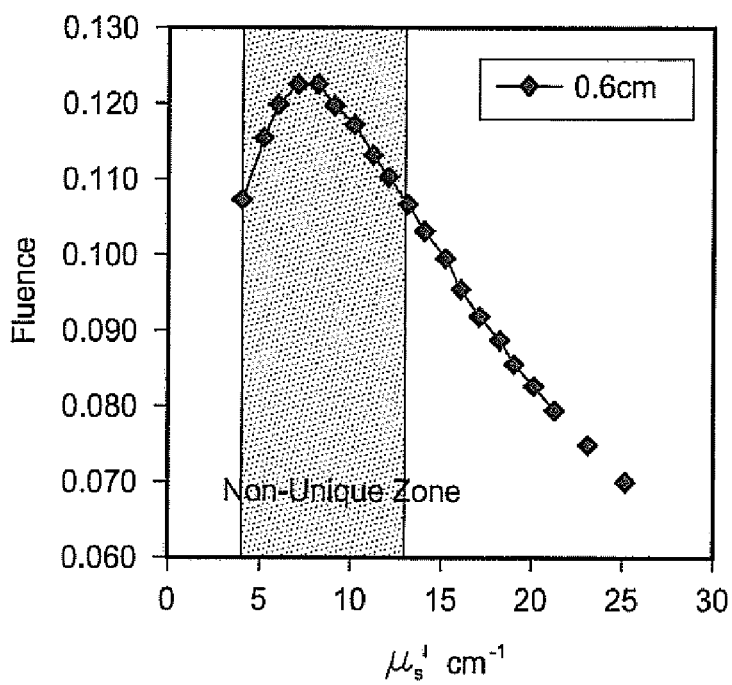
FIG. 12d is a graph of intensity values (reflectance and/or fluence) versus reduced scattering coefficients at detectors spaced 0.6 cm laterally from the emitter, demonstrating the non-monotonic dependence of reflectance (fluence) with reduced scattering coefficients at this lateral emitter-detector separation.
Figure 12E:
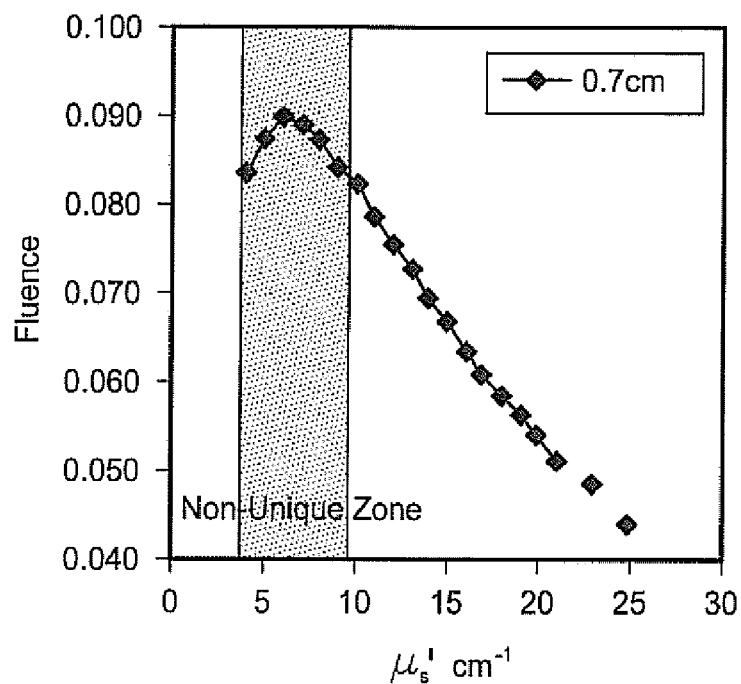
FIG. 12e is a graph of intensity values (reflectance and/or fluence) versus reduced scattering coefficients at detectors spaced 0.7 cm laterally from the emitter, demonstrating the non-monotonic dependence of reflectance (fluence) with reduced scattering coefficients at this lateral emitter-detector separation.
Figure 12F:
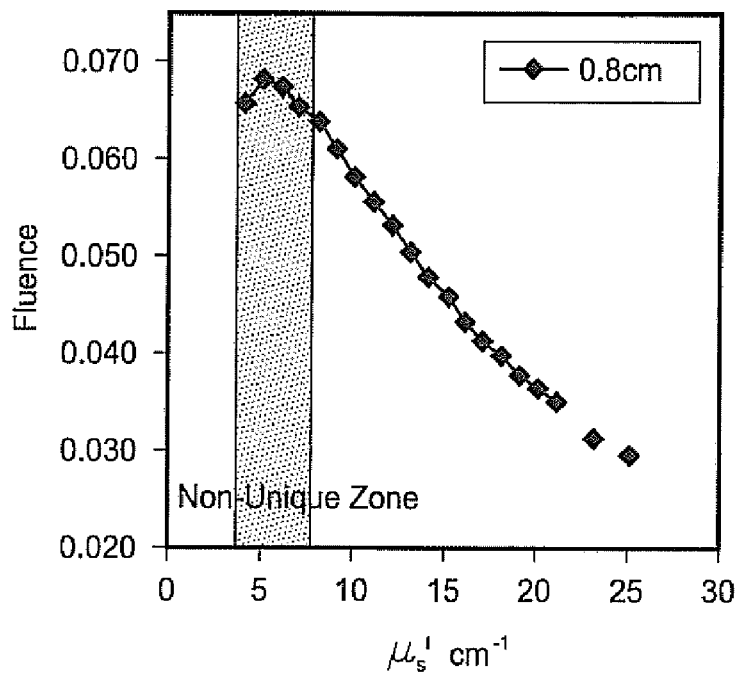
FIG. 12f is a graph of intensity values (reflectance and/or fluence) versus reduced scattering coefficients at detectors spaced 0.8 cm laterally from the emitter, demonstrating the non-monotonic dependence of reflectance (fluence) with reduced scattering coefficients at this lateral emitter-detector separation.

Intensity of propagated light emerging from the tissue surface (i.e., reflectance and/or fluence) in response to the illumination from the emitter is characterized by the scattering and the absorption properties of the tissue. Propagated light intensity measured at detectors 38 located at close proximity to the emitters 36 bear a direct linearly increasing relationship with the reduced scattering coefficient. This linear relationship is illustrated in FIGS. 10-11 with Monte Carlo simulations (FIG. 10) and measurement with Intralipid™ solutions (FIG. 11). Monte Carlo simulations were made with optical properties in physiological ranges to verify the validity of this relationship. Further verification was made with aqueous suspensions of Intralipid™. Bombay ink was used as the absorber. Regression coefficients $R^2$ provided in FIGS. 10-11 indicate the closeness of fit with a linear model.

FIGS. 12*a*-12*f* illustrate relationships between propagated light intensity (i.e., reflectance and/or fluence) and reduced scattering coefficients measured at lateral distances ranging from 3-8 mm from the emitter. It is evident that the relationship is not monotonic, i.e., multiple reduced scattering coefficients at a given absorption coefficient may yield identical values of propagated light intensity. This causes non-uniqueness or absorption and scattering parameter crosstalk, as it is known to a person skilled in the art. This non-uniqueness or crosstalk may appear at all wavelengths, independent of absorber concentrations and specific absorption spectra of analytes. The problem becomes compounded by the fact that, unlike the absorption spectra of various analytes, which have characteristic features including valleys and peaks, the scattering coefficient spectra is generally modeled by a weak exponential and is almost featureless, having little or no valleys and peaks.

Thus, this non-uniqueness can lead to large errors in the determination of optical parameters and therefore analyte concentrations, even when using spectrally-resolved quantification methods. In general, this non-uniqueness is observed at lateral distances of 2-8 mm between the emitter and detector. Reflectance is sensitive to both scattering and absorption changes in the range of lateral distances between 2-8 mm, making scattering and/or absorption coefficients more difficult to accurately determine in this range.

Thus, to address the issue of non-uniqueness, short lateral separations (e.g. less than 2 mm) between the emitters 36 and close-proximity detectors 38 may be used to estimate or calculate the scattering coefficient of the sample and this scattering coefficient information may be used with the diffusion model and light intensity measurements obtained by the far-away detectors 40 to determine analyte concentrations. Propagated light intensity measurements at large separations (e.g., greater than 0.5 cm) are more sensitive to absorption changes and therefore the concentration of specific analytes as compared to those of the scattering coefficient. Note that the phrase "scattering coefficient" as used herein may refer to either a scattering coefficient $\mu_s$ or a reduced scattering coefficient $\mu_s'$, as known in the art.

So measurement of propagated light at short source-detector separations (e.g., <2 mm) gives an initial guess or approximation of scattering coefficients. Then these scattering coefficients may be used as factors in the equations of a diffusion model along with the reflectance values measured at long source-detector separations (e.g., >0.5 cm) to calculate the concentration of analytes. Using scattering coefficients determined through short source-detector separations reduces the number of unknowns in the diffusion model for the long source-detector separations, hence making the solution more accurate. This estimation of scattering coefficients reduces the cross-talk between absorption and scattering coefficients.

It should be noted that relationships described in the earlier paragraph may be restricted to the NIR region of electromagnetic spectra. The absorption in the NIR region of spectra for commonly found analytes in tissue is not significant at the short source-detector separations, as the path length is very small. For example, commonly occurring analytes in tissues may include hemoglobin and myoglobin in blood, water and glucose. The absorption of these analytes is higher in the UV-VIS (200-600 nm) in comparison with NIR (650-1000 nm) range. This permits the use of linear relationships to estimate reduced scattering coefficients using relationships described in FIGS. 10 and 11. Use of the NIR wavelength range also results in a greater penetration depth, which is typically restricted to very superficial regions with the use of illumination in the UV-VIS wavelength range. Thus, the wavelengths used herein may be approximately between 500 to 1350 nm.

In all embodiments of the invention illustrated herein, detectors are at a plurality of different distances from light emitters. In some configurations, more than one detector may be at the same distance from the emitter(s). One or more of the detectors may be placed at close proximity to the emitter(s). The spacing between them may include separate spacers or may be restricted to epoxy resins and buffer/cladding on the optical fibers, if optical fibers are used as emitters and detectors.

The longer this distance, the greater the effect of absorption on scattering coefficient measurements and more prone to non-uniqueness as described in detail earlier. The total number of emitters and detectors may vary. The number of detectors and emitters may be chosen so as to restrict the cost, optimize the design, minimize sophistication, and provide ease of assembly and use. The maximum distance that propagated light can be detected depends upon the optical properties of the tissue and sensitivity of the measurement system. In some embodiments of the invention, distances between the farthest-spaced emitters and detectors can extend up to 2 cm or 3 cm, however shorter or longer distances may be used.

Figure 13:
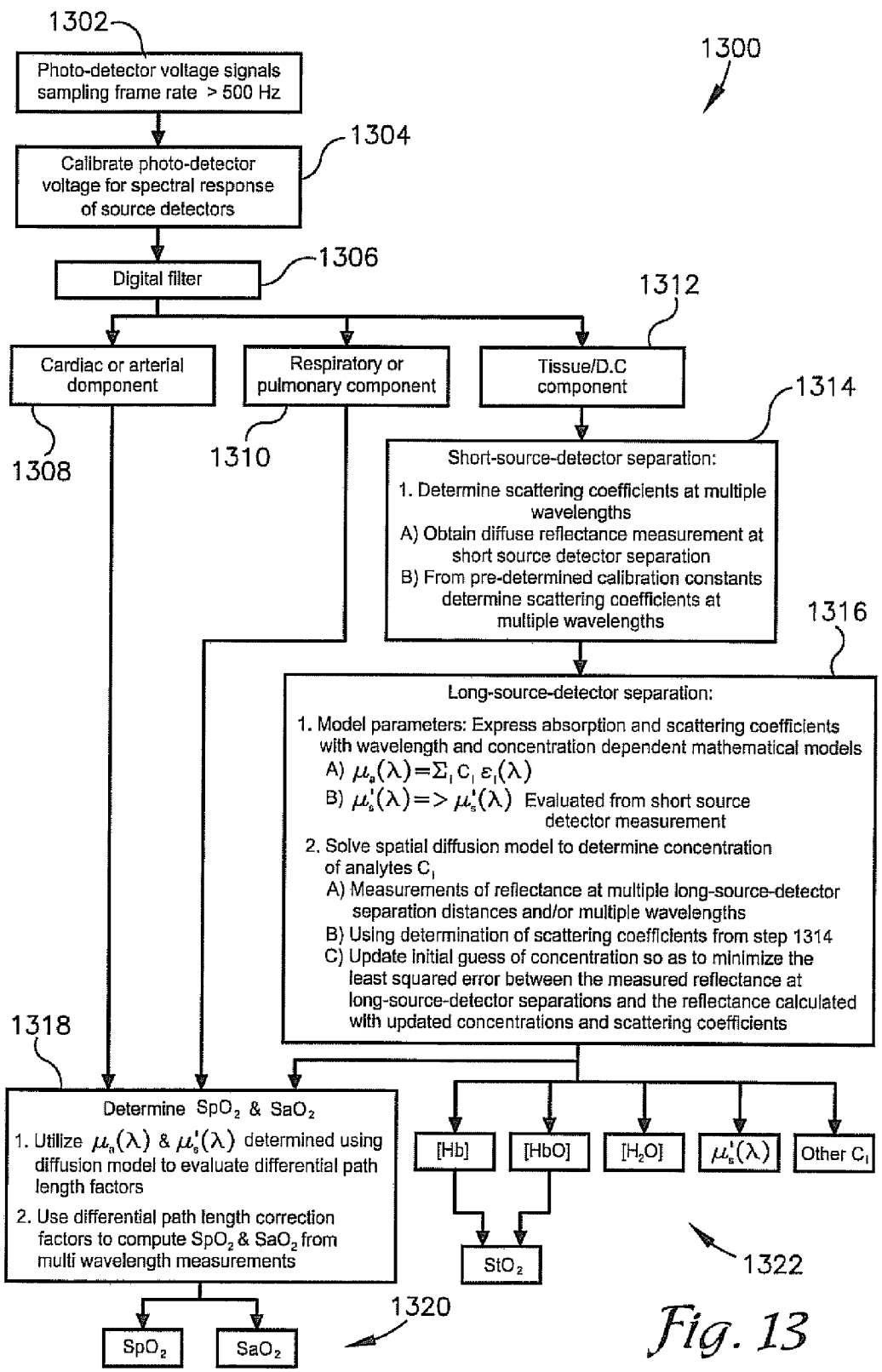
FIG. 13 is a flow chart of a method for quantifying scattering and absorption coefficients and determining analyte concentrations of a sample.

A block diagram of a method for determining concentrations of analytes and scattering coefficients is illustrated in FIG. 13. The flow chart of FIG. 13 depicts the steps of an exemplary method 1300 of the invention in more detail. In some alternative implementations, the functions noted in the various blocks may occur out of the order depicted in FIG. 13. For example, two blocks shown in succession in FIG. 13 may in fact be executed substantially concurrently, or the blocks may sometimes be executed in the reverse order depending upon the functionality involved.

The process of computing analyte concentrations begins by irradiating the tissue with one or more emitters using three or more wavelengths. The choice of wavelengths may depend on the analytes of interest, their expected concentrations, and source-detector separations. The number of wavelengths is chosen such that the number of equations is always greater than the number of unknowns (i.e., scattering coefficients and number of analyte concentrations to be computed). This ensures that the problem is not under-determined (i.e., more unknowns than equations).

As depicted in step 1302, the propagated light though the tissue is collected and/or measured by detectors located at close proximity (short source-detector or emitter-detector separation) and further away (long source-detector or emitter-detector separation) to the emitter(s). This process is a beneficial feature to increase the accuracy of determined parameters as described earlier to meet uniqueness criteria. A time interval between measurements of propagated light intensity is chosen so as to minimize the effect of physiological variations. These variations include but are not limited to heart rate, respiration, vasomotion, and variations due to body movements. For example, a frame rate or sample rate greater than 500 Hz may be chosen. In general, the greater the number of spatially diverse measurements, the more robust and stable is the solution to the spatially resolved diffusion model. The quantity of detectors may be chosen to maximize the accuracy of determination of concentrations without overly increasing the computation burden.

As depicted in step 1304, an algorithm may calibrate the voltages measured by the photo-detectors (may be output from ADC) to account for the non-uniformity in photo-detector responses and/or spectral characteristics of applicable measurement components (optical fibers, photo-detectors, light sources, filters, etc.) using measurements made earlier or alternatively using light source power monitoring components.

As depicted in step 1306, the algorithm may split the measured propagated light signal into frequency bins corresponding to cardiac/arterial components 1308, venous or respiratory components 1310 and tissue or DC components 1312 using a digital filter. Signals are decomposed to frequency components based on their physiological origins. Filters may be implemented either in hardware or software. The filter implementation additionally may consist of components to estimate signal-to-noise ratio and minimize effects due to patient motion or other physiological components that may lead to contamination of propagated light signal components. These signals may alternatively be used to determine heart rate and breathing rate with or without the use of additional physiological/mathematical models. Oxygen saturation for each of these components is determined by methods described below.

As depicted in step 1314, using light intensity values and/or DC components from a detector spaced a short distance from the light source (e.g. less than 2 mm, as defined above), scattering coefficients are calculated or estimated at multiple wavelengths. Scattering coefficients may be determined using measured light intensity and linear calibration parameters previously computed and stored on a memory component of the processing unit 24 and/or 28, as illustrated in FIG. 2. An example algorithm for determining reduced scattering coefficients or scattering coefficients $\mu_s'$ using intensity values of propagated light measured a small source-detector separation is provided in a publication by M. Johns, C. Giller, D. German, and H. Liu, entitled "Determination of reduced scattering coefficient of biological tissue from a needle-like probe," Opt. Express 13, 4828-4842 (2005), incorporated by reference herein in its entirety.

FIG. 14 illustrates one example method for determining scattering coefficients in step 1314 of FIG. 13. As depicted in step 1314a, the tissue/DC component or light intensity is measured at the detector spaced a short distance from the light source. Specifically, as depicted in step 1314b, a plurality of reflectance wavelengths may be measured. Then, as depicted in step 1314c, scattering coefficients are determined for each wavelength separately. In the scattering coefficient equations illustrated in step 1314c, K1 and K2 are calibration parameters which permit direct calibration of reflectance with scattering coefficients. A procedure to determine K1 and K2 is described later in herein.

As depicted in step 1314d, a least square line may then be fit to determine a relationship between reflectance wavelengths and scattering coefficients (computed in step 1314c). As depicted in step 1314e, scattering coefficients computed in step 1314c are compared with those determined with least squares fit in step 1314d. If all scattering coefficients (computed in step 1314c) are found to be within a range of a pre-determined threshold from those computed using the least squares fit, they are fed to the next computational step (step 1316 in FIG. 13) as initial values of scattering coefficients. To reduce the effects of noise, scattering coefficients that are not within the predetermined threshold range may be replaced with those computed using the least squares fit (step

1314d). For example, the allowable range of scattering coefficients in the numerical inversion may be restricted to approximately ±1 cm$^{-1}$ or 10% from the scattering coefficients $\mu_s'$ determined from the intensity values measured by the close proximity detector 38.

Alternatively, scattering coefficients computed in step 1314c may be used directly in step 1314g if it is considered that effects of noise on scattering coefficient determination is insignificant since source-detector separations are very small. Calibration parameters may be periodically updated to maintain accuracy of all computed parameters and account for change in characteristics of the probe apparatus 10, if any. Calibration constants may be modified with changes in specific sites or applications of the measurement head or probe. Alternatively, one set of calibration constants may be used if accuracies of concentrations measured are in a required range.

Determination of calibration coefficients K1 and K2 described in block 1314c of FIG. 14 is carried out prior to application of the probe to a sample being measured. The probe assembly 10 is placed on a medium or sample with known scattering coefficient in the NIR wavelength region of the spectrum. Preferably three or more sets of reflectance measurements, measured at known values of scattering coefficients $\mu_s'$, are used to determine calibration factors K1 and K2 by a simple linear fit. Scattering coefficient $\mu_s'$ values spanning the entire normal physiological ranges should be used to achieve the highest possible accuracy in calibration. Additionally, physical models with known optical properties may be used to verify accuracy of calibration factors and correct for inaccuracies if and when they are found.

In step 1316, illustrated in FIGS. 13 and 15, concentrations of analytes are estimated by iteratively updating an initial approximation of concentrations and scattering coefficients so as to minimize the error between the measured propagated light detected at long source-detector separations and that computed using the diffusion model. In some embodiments of the invention, spatially resolved, steady-state diffuse reflectance models may be used, such as models described in a publication by Farrell et al; A Diffusion Theory Model of Spatially Resolved, Steady-State Diffuse Reflectance for the Noninvasive Determination of Tissue Optical Properties in Vivo, T. J. Farrell, M. S. Patterson, and B. Wilson, Med. Phys. 19, 879 (1992), incorporated by reference herein in its entirety. Alternatively, models described in Absolute Quantification of Deoxyhaemoglobin Concentration in Tissue Near Infrared Spectroscopy, by S. J Matcher and C. E Cooper, Phys. Med. Biol. 39 1295-1312 (1994), incorporated by reference herein in its entirety, may be used.

FIG. 15 illustrates an exemplary method for estimating concentrations of analytes in step 1316 of FIG. 13. An initial approximation of analyte concentrations is determined specific to the application site using physiologically reasonable concentration ranges from previously published data in literature, as depicted in step 1316a. Using a large concentration range may result in an increased number of iterations and hence increased computational time. In order to avoid a needless increase in computation time, reasonable initial approximations and constraints for higher and lower limits of concentrations may be employed. As depicted in step 1316b, an initial approximation of scattering coefficients may be obtained from computations performed in step 1314.

Optical properties (absorption and scattering coefficients) may be described in terms of concentrations and/or wavelength dependent models to reduce the number of unknowns. The number of unknowns does not increase with an increase in the number of wavelengths used and is only dependent on the number of analytes whose concentration is unknown. As depicted in step 1316d, absorption coefficient values at each wavelength are calculated using the initial approximation of the analyte concentrations $C_i$ provided in step 1316a or an updated concentration value $C_i$ from step 1316c, as later described herein. A reflectance or propagated light intensity may be calculated using equations of a diffusion model and information of absorption and scattering coefficients computed in earlier steps, as depicted in step 1316e. For example, the terms $R_1$, $r_2$, D, and $\mu_{eff}$ represent functions of Pa and $\mu_s'$, as known in the art. These terms and their relation to the scattering coefficient $\mu_s'$ and the absorption coefficient $\mu_a$ are further defined in the publication by T. J. Farrell, M. S. Patterson, and B. Wilson entitled A Diffusion Theory Model of Spatially Resolved, Steady-State Diffuse Reflectance for the Noninvasive Determination of Tissue Optical Properties in Vivo, Med. Phys. 19, 879 (1992), incorporated by reference herein in its entirety above.

Squared errors or differences between the computed or calculated propagated light intensity (e.g., using the diffusion model) and actual propagated light intensity (measured at long source-detector separation) are computed, as depicted in step 1316f. If a summation of squared differences is less than a predetermined threshold, as in step 1316g, then all current concentrations $C_i$ and/or scattering coefficients for pulsatile component calculations may be output, as depicted in step 1316h. Otherwise, concentrations of analytes and/or scattering coefficients are updated in successive iterations (as depicted in step 1316c) resulting in a consequent progressive decrease in the mean squared errors. A suitable curve fitting algorithm or numerical optimization method may be used to update the initial approximation of concentrations $C_i$ and scattering coefficients so as to minimize the mean squared errors. During the updating process, the range of scattering coefficients may be restricted to a small range about those determined from the short source-detector separations. For example, as mentioned above, the allowable range of scattering coefficients in the numerical inversion may be restricted to approximately ±1 cm$^{-1}$ or 10% from the scattering coefficients $\mu_s'$ determined from the intensity values measured by the close proximity detector 38.

Iterations of the method illustrated in FIG. 15 may be terminated when errors reach a pre-determined threshold. Infinite loops may be avoided by placing reasonable constraints on the maximum permissible iterations. Suitable thresholds may be chosen to avoid erroneous early convergences and ensure accuracy of analyte concentrations. Most commonly occurring analytes in tissues that may be measured are oxygenated and deoxygenated hemoglobin, myoglobin, glucose & water. In some instances, scattering coefficients may be known (as in step 1314) in fairly close ranges which results in more accurate values of concentrations and significantly fewer iterations to achieve convergence. Constraints, penalty terms, and/or correction factors may be incorporated to only allow a small range of variation of scattering coefficients about those determined using short source-detector separation in step 1314.

Certain checks may be built into the methods described herein order to avoid erroneous convergence, which include and are not limited to restricting concentrations of analytes to physiologically meaningful ranges and restricting permissible values of scattering coefficient to a certain range from those determined in step 1314.

Estimates of steady state concentrations of analytes such as Hb, HbO, water fraction, concentrations of other analytes and scattering coefficients (updated from step 1314) may be determined in step 1322. Other analytes of interest may depend on chosen wavelengths. Absorption and scattering coefficient information determined in step 1316 may be used in step 1318 to determine oxygen saturation of cardiac and respiratory components, as output in step 1320. The analyte concentrations and estimated scattering coefficients of the sample may be used to predict a diagnosis.

In accordance with specific embodiments of the invention, hemoglobin concentration may be computed as a sum of the two hemoglobins, $$Hb_{Total} = Hb + HbO, \quad \text{Equation 1}$$

Where Hb and HbO represent concentrations of oxygenated and deoxygenated hemoglobin. The tissue oxygen saturation $StO_2$, may be determined using the relation:

$$StO_2 = \frac{HbO}{Hb + HbO} \quad \text{Equation 2}$$

In step 1318, oxygen saturation of time-varying components of diffuse reflectance signals may be computed. Absorption and scattering information determined in step 1316 may be used to compute differential path factors. Differential path factors may account for the increase in path length due to light scattering.

Absorption coefficients at a plurality of wavelengths are calculated using the relation, $$\mu_a(\lambda) = \Sigma \epsilon_i(\lambda) C_i \quad \text{Equation 3}$$

Where $C_i$ represents a concentration of analytes, which may include Hb, HbO, and other applicable analytes at the wavelength $\lambda$. $\epsilon_i(\lambda)$ represents the specific absorption of the analyte at the wavelength $\lambda$. Concentrations of analytes determined in step 1316 may be used to determine the absorption coefficients. The differential path length factors may be given by the empirically determined relationship, $$\beta(\lambda) = \frac{1}{2}\sqrt{\left(\frac{3\mu_s'(\lambda)}{\mu_a(\lambda)}\right)}\left(1 - \frac{1}{1 + \rho\sqrt{3\mu_s'(\lambda)\mu_a(\lambda)}}\right) \quad \text{Equation 4}$$

Where $\mu_s'(\lambda)$ is the scattering coefficient determined from short source-detector separations and $\rho$ is the source detector separation distance of the emitter and the detector located further away from each other.

Relative changes of Hb and HbO may be determined from cardiac and respiratory components of multiple wavelength measurements. A ratio of relative change of HbO to the sum of relative change of Hb and HbO yields the saturation of the time varying components. Relative changes in Hb and HbO may be obtained by using Beer-Lambert law-based techniques. It may be assumed that hemoglobin is the predominant absorber in arterial and venous blood. Relative changes in oxygenated and deoxygenated blood concentrations may be given by, $$\begin{bmatrix} \Delta Hb \\ \Delta HbO \end{bmatrix} = [\epsilon]^{-1}\left[\frac{1}{\beta(\lambda)}R(\lambda)\right] \quad \text{Equation 5}$$

Where $\epsilon$ denotes the matrix of specific absorption coefficients for all wavelengths, $\beta(\lambda)$ denotes the differential path factor computed in Equation 4 and $R(\lambda)$ denotes the column vector of logarithm of a ratio of ac intensity to dc intensity. Further, $$SO_2 = \frac{\Delta HbO}{\Delta HbO + \Delta Hb} * 100\% \quad \text{Equation 6}$$

Where $SO_2$, would be denoted $SpO_2$ or $SaO_2$ depending on the component used to determine relative changes in Hb and HbO.

Checks may be built into the methods described herein to ensure accuracy of computed parameters and reduce erroneous alarms. $SpO_2$ and $SaO_2$, depicted in step 1320, may be logged at every frame.

Additionally, step 1318 may include techniques that utilize information computed in steps 1314 and 1316. These methods may include use of light scattering coefficients and/or concentration of analytes determined in step 1316. These parameters may be used to correct for errors related to motion or other physiologically caused artifacts in determination of arterial or venous blood oxygen saturations. Additionally, they may be used to make a decision on whether a particular alarm has to be invoked.

In a case of continuous monitoring, the computational steps or computational blocks illustrated in FIGS. 13-15 may be executed repeatedly and parameter values may be logged at the end of an iteration for retrieval later and for tracking computing trends. These trends may be used for diagnostic purposes as desired.

The steps of the methods in FIGS. 13-15 may be computational blocks of the apparatuses described herein. The methods describe one of the possible methods to determine analyte concentrations and scattering coefficients with increased accuracy. In one embodiment, numerical inversion of a single layer diffusion equation may be used to determine concentrations.

Alternatively, more complex models of light propagation in tissue may be employed to evaluate a layer-wise concentration of analytes. Further, these techniques may be used to determine topographic and/or tomographic maps and functional images of concentrations in tissues.

One specific alternate embodiment may include the use of intensity modulated sources and detectors. The analyte concentration and scattering coefficient information obtained from the technique described in FIGS. 13-15 may be used to compute layer-wise concentration of analytes as described. Accurate initial estimates of superficial layer parameters not only provide better estimates of deeper layer parameters but also accelerate the rate of convergence of iterative algorithms (such as the diffusion model) thereby decreasing the detection time.

The methods described above use measurements and calculations performed in the continuous domain. However, the described technique may also be utilized to augment and improve estimates of scattering coefficients and analyte concentrations determined using frequency or time domain techniques. A specific example of such utilization may include generation of initial estimates of scattering coefficients and analyte concentrations to iteratively or non-iteratively solve complex multilayer time-dependent light propagation models to determine scattering coefficients and analyte concentrations specific to layers in the tissue or sampled turbid media.

FIG. 16 illustrates an exemplary method for determining multilayer concentrations of analytes and scattering coefficients. Scattering coefficient information (using a source-detector at close proximity as in steps 1602 and 1608) by itself or analyte concentration information from far source detector separation (as depicted in step 1604) or both (as depicted in step 1610) may be used as initial information to solve multi-layer frequency and time domain models of light propagation (as depicted in step 1612) to determine layer-wise scattering coefficients and analyte concentration information (as depicted in steps 1614, 1616, and 1618). As depicted in step 1606, intensity modulation and phase measurement information after light propagation may also be required by step 1612. Multi-layer frequency and time domain models similar to those in a publication by A. Kienle et al. may be used to determine the multilayer concentration of analytes and scattering coefficients. Specifically, the publication by A. Kienle et al. is "Noninvasive Determination of the Optical Properties of Two-Layered Turbid Media," Appl. Opt. 37, 779-791 (1998), by Alwin Kienle, Michael S. Patterson, Nora Dögnitz, Roland Bays, Georges Wagnivres, and Hubert van den Bergh, incorporated by reference herein in its entirety.

Although the invention has been described with reference to the preferred embodiment illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following.

The invention claimed is:

1. A method to determine the concentration of analytes in tissues and samples, the method comprising:
   a. illuminating a tissue or a sample with a plurality of light wavelengths with one or more light emitters;
   b. measuring intensity values of light propagated from the tissue or sample at a plurality of distances from the one or more light emitters with at least one detector configured for detecting light, wherein light is measured at a first lateral distance and at a second lateral distance, wherein the first lateral distance is smaller than the second lateral distance;
   c. calculating one or more scattering coefficients $\mu_s'$ for the plurality of light wavelengths based on the light intensity values measured at the first lateral distance independent of light intensity values measured at the second lateral distance; and
   d. calculating analyte concentrations using one or more of the scattering coefficients $\mu_s'$ and using the intensity values at the plurality of light wavelengths measured at the second lateral distance without calculating scattering coefficients for the plurality of wavelengths based on the light intensity values measured at the second lateral distance.

2. The method of claim 1, wherein the light wavelengths are in the range of about 500-1350 nm.

3. The method of claim 1, wherein the scattering coefficients are determined in the continuous domain.

4. The method of claim 1, wherein step d comprises calculating a numerical inversion of a diffusion model with the scattering coefficients calculated in step c and the propagated light intensity measured at the second lateral distance at the plurality of wavelengths.

5. The method of claim 4, wherein absorption coefficients $\mu_a$ of the tissue or sample are calculated using an approximation of analyte concentrations.

6. The method of claim 5, further comprising:
   using the scattering coefficients $\mu_s'$ and the absorption coefficients $\mu_a$ in the diffusion model to determine one or more calculated intensity values of propagated light;
   comparing the calculated intensity values of propagated light with the measured intensity values of propagated light measured at the second lateral distance; and
   iteratively updating the approximation of analyte concentrations and determining the calculated intensity values of propagated light using the updated approximation of analyte concentrations until the calculated intensity values are within a specified range of the measured intensity values.

7. The method of claim 6, outputting a current value of the approximation of analyte concentrations once the calculated intensity values are within the specified range of the measured intensity values measured at the second lateral distance.

8. The method of claim 1, wherein the first distance is equal to or less than about 2 mm and the second distance is equal to or greater than about 0.5 cm.

9. The method of claim 1, further comprising calculating arterial and venous blood oxygen saturations using the estimated scattering coefficients at the plurality of wavelengths and the calculated analyte concentrations.

10. The method of claim 4, wherein step c of calculating the scattering coefficients $\mu_s'$ further comprises fitting a line through the scattering coefficients $\mu_s'$ calculated from the intensity values measured at the first lateral distance at the plurality of wavelengths and restricting all of the scattering coefficients $\mu_s'$ within a range of plus or minus approximately 1 cm$^{-1}$ or approximately 10% from the line.

11. The method of claim 1, wherein a plurality of intensity measurements are used to calculate the one or more scattering coefficients $\mu_s'$ and the plurality of intensity measurements are obtained at several different locations relative to the one or more emitters with each of the several different locations spaced the first lateral distance away from the one or more emitters.

12. A method to determine the concentration of analytes in tissues and samples, the method comprising:
   a. illuminating a tissue or a sample with a plurality of light wavelengths in the range of 500-1350 nm with one or more light emitters;
   b. measuring intensity values of light propagated from the tissue or sample at a plurality of distances from the one or more light emitters with one or more light detectors, wherein light is measured at a first lateral distance and at a second lateral distance, wherein the first lateral distance is smaller than the second lateral distance;
   c. calculating one or more scattering coefficients $\mu_s'$ for the plurality of wavelengths using the intensity values measured at the first lateral distance; and
   d. calculating a numerical inversion of a diffusion model using one or more of the scattering coefficients $\mu_s'$ and the measured intensity values of propagated light measured at the second lateral distance to determine the concentration of analytes in the tissue or sample.

13. The method of claim 12, wherein the first lateral distance is less than about 2 mm and the second lateral distance is greater than about 0.5 cm.

14. The method of claim 12, wherein the first lateral distance is less than about 1.3 mm and the second lateral distance is greater than 0.7 cm.

15. The method of claim 12, further comprising evaluating differential path length factors using the scattering coefficients $\mu_s'$ and absorption coefficients calculated using the analyte concentrations and comprising computing SpO$_2$ and SaO$_2$ based on the differential path length factors.

16. The method of claim 12, further comprising using the analyte concentrations to determine at least one of Hb, HbO, HbA1c, StO$_2$, and H$_2$O.

17. The method of claim 12, wherein the detectors measure the propagated light in the continuous domain and determine the scattering coefficients $\mu_s'$ using continuous domain measurements.

18. The method of claim 12, wherein calculating the numerical inversion of the diffusion model comprises:

using one or more of the scattering coefficients $\mu_s'$ and an initial approximation of analyte concentrations as factors in one or more diffusion model equations to determine one or more calculated intensity values of propagated light;

iteratively updating the initial approximation of analyte concentrations and recalculating the calculated intensity values until the calculated intensity values and the measured intensity values measured at the second lateral distance are within a pre-determined range of each other; and outputting a current updated value of the initial approximation of analyte concentrations when the calculated intensity values are within the predetermined range of the measured intensity values measured at the second lateral distance.

19. A method to determine analyte concentrations in a tissue or sample, the method comprising:

a. illuminating the tissue or sample with a plurality of light wavelengths in the range of 500-1350 nm with one or more light emitters;

b. measuring intensity values of propagated light from the tissue or sample at a plurality of lateral distances from the one or more emitters with one or more light detectors, wherein at least one of the distances is less than about 2 mm and at least one of the distances is greater than about 1 cm;

c. calculating one or more scattering coefficients $\mu_s'$ at the plurality of wavelengths determined from the intensity values measured at less than about 2 mm; and d. calculating analyte concentrations using one or more of the scattering coefficient $\mu_s'$ and using the intensity values measured for the plurality of wavelengths at a distance greater than about 1 cm.

20. The method of claim 19, wherein the detectors comprise one or more photo detectors located away from the tissue or sample and light reflected from the tissue or sample is collected through one or more optical fibers and transmitted to the one or more photo detectors, wherein each end of the optical fibers is laterally located at less than 2 mm from the one or more light emitters or greater than 1 cm from the one or more light emitters.

* * * * *